US006576620B2

(12) United States Patent
Belardinelli et al.

(10) Patent No.: US 6,576,620 B2
(45) Date of Patent: Jun. 10, 2003

(54) METHOD OF IDENTIFYING PARTIAL ADENOSINE A1 RECEPTOR AGONISTS

(75) Inventors: Luiz Belardinelli, Menlo Park, CA (US); Zhenhai Gao, San Jose, CA (US)

(73) Assignee: CV Therapeutics, Inc., Palo Alto, CA (US)

(*) Notice: Subject to any disclaimer, the term of this patent is extended or adjusted under 35 U.S.C. 154(b) by 0 days.

(21) Appl. No.: 09/728,555

(22) Filed: Dec. 1, 2000

(65) Prior Publication Data

US 2001/0008883 A1 Jul. 19, 2001

Related U.S. Application Data

(63) Continuation-in-part of application No. 09/454,485, filed on Dec. 3, 1999, now Pat. No. 6,294,522, and a continuation-in-part of application No. 09/454,436, filed on Dec. 3, 1999, now Pat. No. 6,258,793, and a continuation-in-part of application No. 09/454,136, filed on Dec. 3, 1999.

(60) Provisional application No. 60/168,873, filed on Dec. 3, 1999, provisional application No. 60/220,125, filed on Jul. 21, 2000, and provisional application No. 60/220,127, filed on Jul. 21, 2000.

(51) Int. Cl.$^7$ ........................ C07H 19/167; A61K 31/70
(52) U.S. Cl. ........................ 514/46; 514/47; 536/27.61; 536/27.62; 536/27.63; 435/7.1
(58) Field of Search ................... 514/46, 47; 536/27.61, 536/27.62, 27.63; 435/7.1

(56) References Cited

U.S. PATENT DOCUMENTS

| | | | | |
|---|---|---|---|---|
| 4,364,922 A | * | 12/1982 | Berne et al. | 514/46 |
| 4,373,097 A | * | 2/1983 | Stramentinoli et al. | 536/27.6 |
| 4,673,563 A | * | 6/1987 | Berne et al. | 514/46 |
| 5,104,859 A | * | 4/1992 | Sollevi | 514/46 |
| 5,446,046 A | * | 8/1995 | Belardinelli et al. | 514/263 |
| 5,589,467 A | * | 12/1996 | Lau et al. | 514/46 |
| 5,631,260 A | * | 5/1997 | Belardinelli et al. | 514/263 |
| 5,736,528 A | * | 4/1998 | Belardinelli et al. | 514/46 |
| 5,789,416 A | * | 8/1998 | Lum et al. | 514/261 |
| 5,998,387 A | * | 12/1999 | Belardinelli et al. | 514/46 |
| 6,258,793 B1 | * | 7/2001 | Palle et al. | 514/46 |
| 6,294,522 B1 | * | 9/2001 | Zablocki et al. | 514/46 |

FOREIGN PATENT DOCUMENTS

| | | | |
|---|---|---|---|
| WO | W O 99/24450 A2 | * | 5/1999 |
| WO | W O 99/24451 A2 | * | 5/1999 |

OTHER PUBLICATIONS

Roelen, H. et al, "N6, C8-Distributed Adenosine Derivatives as Partial Agonists for Adenosine A1 Receptors", *Journal of Medicinal Chemistry*, vol. 39 (1996) p. 1463–1471.

Van Der Wenden, et al., "5-Substituted Adenosine Analogs as New High-Affinity Partial Agonists for the Adenosine A1 Receptor", *Journal of Medicinal Chemistry*, vol. 41 (1988) p. 102–108 (Jan. 1, 1998).

Lorenzen, et al., "Activation of Various Subtypes of G–protein alpha Various Subtypes of G–protein alpha subunits by Partial Agonists of the Adenosine A1 Receptor", *Biochemical Pharmacology*, vol. 56 (1998), p. 1287–1293.

Hutchinson et al., "Adenosine Receptor Ligands with Oxygenated $N^6$–Substituents," *Bioorganic & Medicinal Chemistry Letters*, 9(7), 933–936 (Apr. 5, 1999).*

Snowdy et al., "A Comparison of an $A_1$ Adenosine Receptor Agonist (CVT–510) with Diltiazem for Slowing of AV Noval Conduction in Guinea–Pig," *British Journal of Pharmacology*, 126(1), 137–146 (1999).*

Snowdy et al., "A Comparison of an $A_1$ Adenosine Receptor Agonist (CVT–510) with Diltiazem for Slowing of AV Nodal Conduction on Guinea–Pig," *British Journal Pharmacology*, 126(1), 137–146 (1999).*

Watson et al., "Adenosine and Adenine Nucleotides," in Section I of *The G–Protein Linked Receptor FactsBook*, Academic Press, New York, NY, 1994, only pp. 19–31 supplied.*

Williams, M., "Adenosine Receptor—An Historical Perspective," Chapter 1 in *Adenosine and Adenosine Receptors*, M. Williams (ed.), The Humana Press, Clifton, NJ, 1990, only pp. 1–15 supplied.*

Williams et al.(I), "Radioligand Binding Assays for Adenosine Receptors," Chapter 2 in *Adenosine and Adenosine Receptors*, M. Williams (ed.), The Humana Press, Clifton, NJ, 1990, only pp. 17–55 supplied.*

Trivedi et al., "Structure–Activity Relationships of Adenosine $A_1$ and $A_2$ Receptors," Chapter 3 in *Adenosine and Adenosine Receptors*, M. Williams (ed.), The Humana Press, Clifton, NJ, 1990, only pp. 57–103 supplied.*

Williams et al. (II), "Adenosine Receptor Ligands As Therapeutic Entities: Molecular Specificity In Relation to Functional and Therapeutic Activity," published in *Adenosine Receptors in the Nervous System*, J. A. Ribeiro (Ed.), Taylor & Francis, New York, NY, 1989, only pp. 61–68 supplied.*

Mullane et al., "Adenosine and Cardiovascular Function," Chapter 8 in *Adenosine and Adenosine Receptors*, M. Williams (ed.), The Humana Press, Clifton, NJ, 1990, only pp. 17–55 supplied.*

M. G. Collis, "Influence of Adenosine on Cardiac Activity," Chapter 20 in *Adenosine and Adenine Nucleotides as Regulators of Cellular Function*, J. W. Phillis (ed.), CRC Press, Boca Raton, FL, 1991, only pp. 249–257 supplied.*

Venes et al. (eds.), *Taber's Cyclopedic Medical Dictionary, 19th Edition*, F. A. Davis Co., Philadelphia, PA, 2001, only pp. 419 and 1103 supplied.*

(List continued on next page.)

Primary Examiner—James O. Wilson
Assistant Examiner—Lawrence E Crane
(74) Attorney, Agent, or Firm—McDonnell Boehnen Hulbert & Berghoff

(57) ABSTRACT

The present invention provides a method for identifying partial adenosine A1 receptor agonists that are useful in the treatment of arrhythmias. Partial adenosine A1 receptor agonists and methods for using partial adenosine A1 receptor agonists to treat arrhythmias in mammals.

8 Claims, 3 Drawing Sheets

OTHER PUBLICATIONS

Beers et al. (eds.), *The Merck Manual of Diagnosis and Therapy, 17th Edition*, Merck & Col., Whitehouse Station, NJ, 1999, only pp. 1721–1730 supplied.*

Huang et al., "Ventricular Arrhythmias Induced by Chemically Modified Intrinsic Cardiac Neurons," *Cardiovascular Research*, 28(5), 636–642 (1994).*

Miyatake et al., "Adenosine Mediates the Antiarrhythmic Effects of Ischemic Preconditioning in Isolated Rat Hearts," *Jpn. Circ. Journal*, 60(6), 341–348 (1996); *Chemical Abstracts*, 125(19), p. 99, Abstract No. 238103k (Nov. 4, 1996); only abstract supplied.*

* cited by examiner

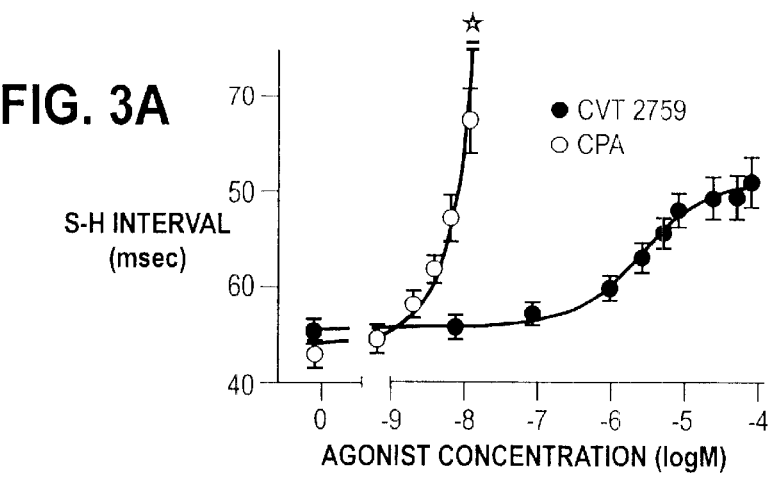
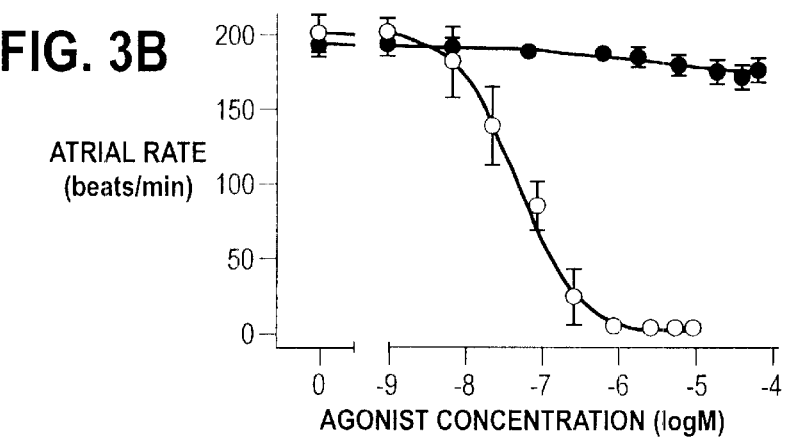
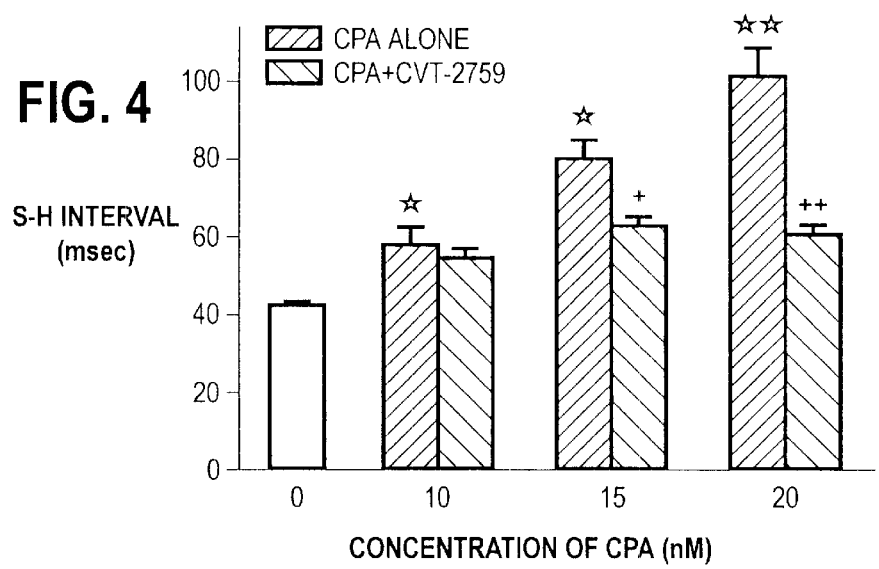

METHOD OF IDENTIFYING PARTIAL ADENOSINE A1 RECEPTOR AGONISTS

This invention is entitled to claim the benefit of the filing dates of Provisional Patent Application Seril Nos. 60/168,873, filed Dec. 3, 1999, 60/220,125 filed Jul. 21, 2000, and 60/220,127 filed on Jul. 21, 2000 and this application is a continuation in part of each of the following co-pending U.S. patent application Ser. No. 09/454,485 filed Dec. 3, 1999, now U.S. Pat. No. 6,294,522, U.S. patent application Ser. No. 09/454,436 filed Dec. 3, 1999, now U.S. Pat. No. 6,258,793 and U.S. patent application Ser. No. 09/454,136 filed Dec. 3, 1999.

BACKGROUND

1. Field of Invention

This invention relates to a method of identifying compounds with partial adenosine A1 receptor activity, compounds with partial A1 agonist activity identified by the method, and a method of treating arrhythmias in mammals comprising administering an effective amount of a partial Adenosine A1 receptor agonist to a mammal in need of such treatment.

2. Description of the Art

Atrial arrhythmias, such as primary atrial fibrillation, atrial flutter and paroxysmal atrial tachycardia, are largely due to the rapid transmission of electrical impulses through the AV node, a critical regulator of heart rate. Prompt slowing of this rapid AV nodal conduction is often the immediate goal of treatment to slow the abnormally rapid heart rate.

Arrhythmias are treated with a variety of compounds including adenosine, a naturally occurring compound that has a wide variety of physiological and pharmacological effects. The biological effects of adenosine are mediated by interaction with several adenosine receptor subtypes known as known as adenosine A1, A2A, A2B, and A3.

Adenosine has proven effective in terminating paroxysmal supraventricular tachycardia (PSVT) due to its negative dromotropic effects on the atrioventricular (AV) node. These effects, which are primarily related to activation of $I_{KAdo}$ and to a lesser extent $I_{Ca(L)}$, are short-lived because adenosine's half-life is less than 10 sec. Adenosine, although highly effective in terminating PSVT, is limited in the treatment of rate control during atrial fibrillation because of its ultra short half-life (~10 sec), vasodilatory effects, and its direct effects on sympathetic tone. Longer acting non-selective stable adenosine derivatives could circumvent this shortcoming, but on the other hand, could be potentially harmful due to deleterious effects mediated through activation of the A2A, A2B, and the A3 adenosine receptor subtypes, which mediate coronary vasodilatation, systemic vasodilatation and mast cell degranulation.

Other groups of antiarrhythmic compounds are presently available for intravenous use to control rapid ventricular rates during atrial fibrillation but all have significant limitations. Digoxin has a delayed onset of action (~30 min) and its peak effects are not observed for 3 to 4 hours after its administration. β-blockers and calcium-channel blockers have a quicker onset of action but their hypotensive and negative inotropic effects may have adverse consequences.

Thus, there is a need for a method of treating arrhythmias with pharmacologic agents that are selective, easy to administer, well-tolerated, have sufficiently long half-lives, and are rapidly efficacious.

SUMMARY OF THE INVENTION

It is an object of this invention to provide a method to identify desirable compounds for treating arrhythmia. Desireable compounds are selective to the A1 receptor, have dose dependent negative dromotrophic effects while not affecting sinus rate or blood pressure.

A further object of this invention are partial A1 receptor agnonists having the desired properties, that have activity as partial adenosine A1 receptor agonists, that are useful in the treatment of arrhythmias and that lack the side effects of conventional treatments.

Another object of this invention is a method for identifying compounds that act as partial adenosine A1 receptor agonists.

An still further object of the invention is a method of predicting the ability of agonists to act as partial adenosine A1 receptor agonists.

In one embodiment, this invention includes a method of identifying partial Adenosine A1 receptor agonists comprising determining level of agonist stimulated $[^{35}S]GTP\gamma S$ binding to G proteins of a compound and comparing its response to that a full agonist. Preferably, compounds that stimulate less than 65% $[^{35}S]GTP\gamma S$ binding of the full agonist are eliminated. Compounds that behave as full agonists, that is that stimulate greater than 90% of the $[^{35}S]GTP\gamma S$ binding of the full agonist are also eliminated. Then compounds preferably having at least 75% of the $[^{35}S]GTP\gamma S$ binding activity of a full agonist are selected.

The binding affinities of the the subgroup of remaining compounds (i.e. those with at least 65% of the binding activity of the full agonist, are evaluated. Compounds having a low binding affinity, that is $K_i$ less than 3 uM are selected. Preferred compounds of the invention will have a $K_i \leq 1$ uM.

In another embodiment, this invention includes a method of predicting the effect of compounds on in-vivo activities mediated by the adenosine A1 preferrably those in heart.

Is still another embodiment, this invention includes partial adenosine A1 receptor agonists identified by the methods of the invention.

In a further embodiment, this invention includes a method for treating arrhythmias, such as primary atrial fibrillation, atrial flutter and paroxysmal atrial tachycardia, with a partial adenosine A1 receptor agonist.

DESCRIPTION OF THE FIGURES

FIG. 3. Concentration-response relationships for the negative dromotropic (increase of S-H interval, top panel) and negative chronotropic (decrease of atrial rate, bottom panel) actions of Compound 6 of Example 2 and CPA. Experimental measurements of atrial rate and S-H interval were done on different hearts (see Methods for protocols). In the top panel each point represents the mean and SEM of single determinations in each of 4–12 hearts for Compound 6 of Example 2 and 4 hearts for CPA. In the bottom panel each point represents the mean and SE of single determinations in each of 5 hearts for Compound 6 of Example 2 and 4 hearts for CPA.

*, second-degree AV block occurred in all hearts in the presence of 30 nM CPA

FIG. 4. Attenuation by the partial agonist Compound 6 of Example 2 (10 $\mu$M) of the increase of S-H interval caused by the fall agonist CPA (10, 15, and 20 nM). In each experiment a control S-H interval (0 CPA) and the response to a single concentration of CPA (in the absence and presence of 10 $\mu$M Compound 6 of Example 2) was measured. Bars indicate the mean and SE of single determinations in each of 4 (presence of CPA) or 12 hearts (absence of CPA).

Figure 5:
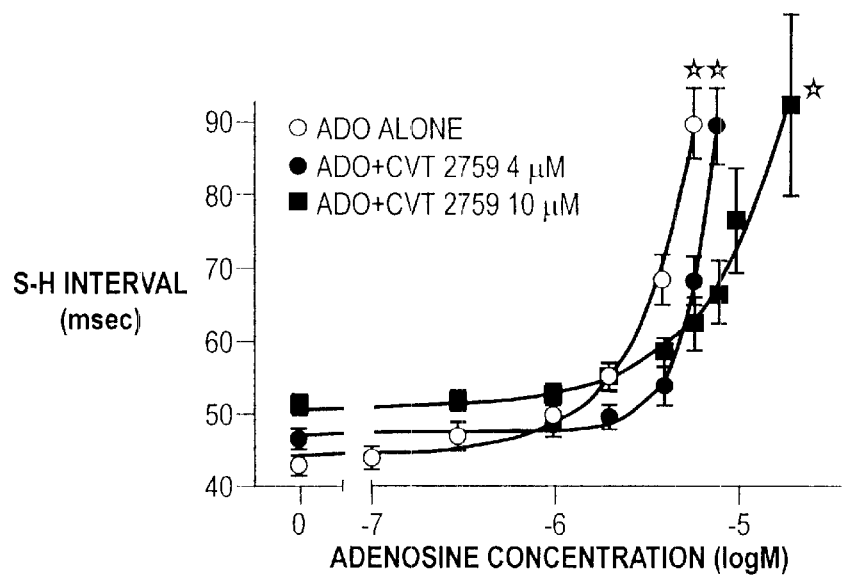

*, **, $p<0.05$ and $p<0.01$, respectively, compared to control by ANOVA and Dunnett's test +, ++, $p<0.05$ and $p<0.01$, respectively, compared to CPA alone, by paired t-test FIG. 5. Attenuation by Compound 6 of Example 2 (4 and 10 $\mu$M) of the action of adenosine to increase the S-H interval of the guinea pig isolated heart. In the presence of Compound 6 of Example 2 the concentration-response relationship for adenosine to increase the S-H interval was shifted to the right. Points indicate the mean and SE of single determinations in each of 4–5 hearts.

*, A-V block occurred at concentrations higher than those shown here

Figure 6:
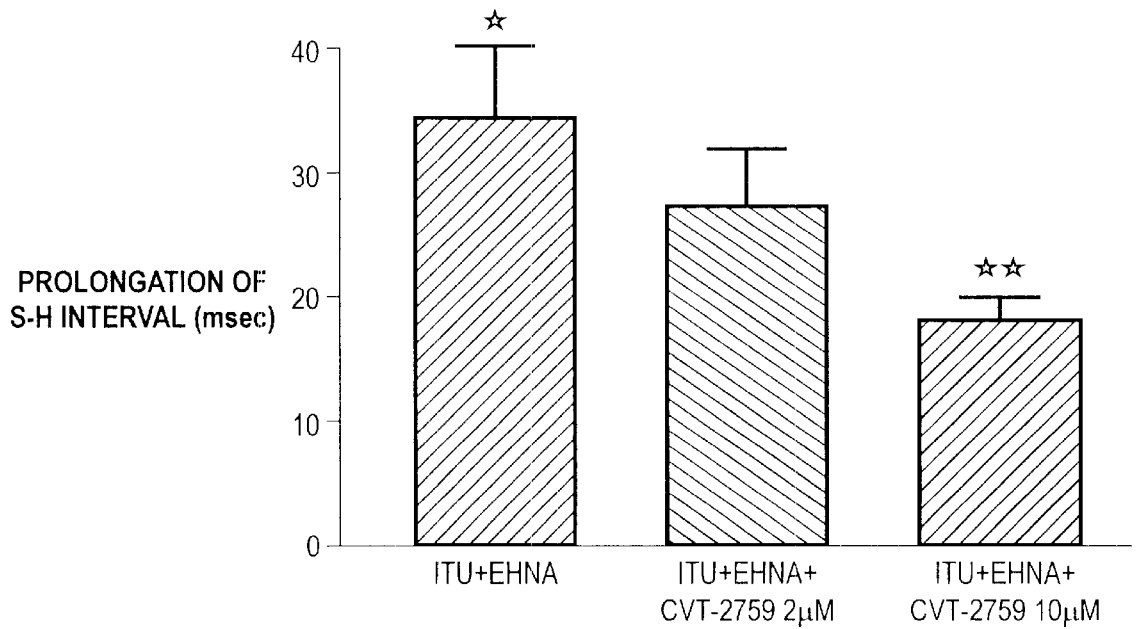

FIG. 6. Attenuation by Compound 6 of Example 2 of the prolongation of S-H interval of the guinea pig isolated heart caused by the combination of iodotubercidin (ITU, 1 $\mu$M) and EHNA (200 nM). Simultaneous administration of ITU and EHNA increased significantly the concentration of adenosine in the coronary effluent (see text). Bars indicate values of the mean and SE of single determinations in each of 6 hearts. The S-H interval in the absence of compound (control) was 46±1 msec.

*, $p<0.001$ compared to control

**, $p<0.01$ compared to ITU +EHNA

ABBREVIATIONS $A_1$-AdoR, $A_1$-adenosine receptor; ADA, adenosine deaminase; AV, atrioventricular; CCPA, 2-chloro-$N^6$-cyclopentyladenosine; CHA, $N^6$-cyclohexyladenosine; CPA, $N^6$-cyclopentyladenosine; CPT, 8-cyclopentyl-1,3-dimethylxanthine; CPX, 8-cyclopentyl-1,3-dipropylxanthine; CVT-2759, [(5-{6-[((3R)oxolan-3-yl)amino]purin-9-yl}(3S,2R,4R)-3,4-dihydroxyoxolan-2-yl)methoxy]-N-methylcarboxamide; CVT-510, $N^6$-[3-R-tetrahydrofuranyl]amino-purine riboside; EHNA, erythro-9-(2-hydroxy-3-nonyl)adenine; FRTL-5, Fischer rat thyroid line-5; G-protein coupled receptor, GPCR; ITU, iodotubercidin; $K_d$, equilibrium dissociation constant; $K_i$, dissociation constant of a competitive inhibitor; K-H, Krebs-Henseleit; KRH, Krebs-Ringer HEPES; S-H, stimulus-to-His bundle.

DESCRIPTION OF THE CURRENT EMBODIMENT

This invention provides methods for identifying partial adenosine A1 receptor agonists for use in the treatment of arrhythmias, and methods for predicting in-vitro and in vivo activity of partial adenosine receptor agonists. This invention also provides partial A1 receptor agonists as well as methods for using partial A1 receptor agonsist to treat arrhythmias in mammals and especially in humans.

An important concept for understanding the invention is the means by which adenosine agonists interact with a receptor and thereby regulates cellular activities. All adenosine receptor agonists bind to the extracellular domain of protein, known as a G-protein coupled receptor (GPCR) that is a member of superfamily of seven transmembrane molecules. GPCRs are so named because the intracellular domains of the receptor are coupled to G proteins, which are heterotrimeric molecules consisting of an $\alpha$ subunit bound to both a molecule of GDP and to a $\beta$ and $\gamma$ subunit. When agonists bind to the adenosine receptor the guanylnucleotide binding site on the G-protein is altered allowing GTP to bind in place of GDP. The binding of GTP causes the $\alpha$ subunit to dissociate from the by subunit allowing the $\alpha$ to bind to adenlyl cyclase. The consequent activation or inhibition of adenyl cyclase hydrolysizes a molecule of ATP thus producing cAMP. cAMP, an important intracellular mediator, acts as an allosteric effector to activate specific proteins thereby modulating the biological activity of a cell. Hydrolysis of the GTP by the $\alpha$ subunit restores the subunit to its orignal conformation, causing it to dissociate from the adenyate cyclase (which becomes inactive) and to reassociate with the $\beta\gamma$ complex.

The activity of an agonist in stimulating GPCR such as the adensosine A1 receptors can be measured by virtue of the guanine nucleotide exchange which provides a direct measurement of receptor-dependent G protein activation. This activation is assayed using radiolabled GTP or GTP analogs. In particular, the GTP analog guanosine 5'-O-(3-[$^{35}$S] thiotriphophate [$^{35}$S]GTPγS which has a high affinity for G proteins and a resistance to GTPase activity, has been useful for studying adenosine receptor. [$^{35}$S]GTPγS binding assays also have several advantages over other radioligand-binding assays, they are rapid, easy to automate, and amenable to high throughput screening.

[$^{35}$S]GTPγS binding reflects the intrinisic efficacy associated with therapeutic compounds. A compound with high intrinisc efficacy evokes the maximal effect of which the biological system is capable. These compounds, known as full agonists, are able to elicit the maximum possible effect without occupying all the receptors if the efficiency of coupling to the effector process is high. Partial agonists evoke a response but cannot evoke the maximal response of which the biological system is capable, despite occupying all available receptors. They may have reasonable affinity but low intrinsic efficacy.

The intrinsic efficacy of a given compound may vary from cell type to cell type and/or from effector system to effector system. As defined herein, a "full agonist" is a compound that binds to a receptor and elicits a maximal response. Thus, a compound that has an intrinsic efficacy lower than a full agonist (i.e. submaximal) is called a partial agonist. The term "partial agonist", as used herein, is a molecule that binds to a receptor and elicits a response that is smaller than that of a full agonist (submaximal), but also competitively antagonizes the response(s) elicited by a full agonist. Many full agonists of the adenosine A1 receptor are known to those skilled in the art an example being $N^6$-cyclopentyladenosine (CPA).

A compound is also defined by its potency. Potency is the dose or concentration required bring about some fraction of a compound's maximal effect (i.e., the amount of compound needed to produce a given effect. In graded dose-response measurements, the effect usually chosen is 50% of the maximum effect and the dose causing the effect is called the $EC_{50}$. Potency is determined mainly by the affinity of the receptor for the compound. A compound may be potent but have a smaller intrinisc activity than another compound. Relatively potent therapeutic compounds are preferrable to weak ones in that lower concentrations produced the desired effect thereby circumventing the effect of concentration dependent side-effects.

The binding affinity of a compound is evaluated in a competitive binding assay. A radiolabeled adenosine A1 antagonist, known as astritiated 8-cyclopentyl-1,3-dipropyl [2,3-3H(N)]xanthine ([$^3$1H]CPX) binds to guinea pig forebrain membranes. In the presence of a full agonist, such as CPA, and a putative partial agonist, such as Compound 6 of Example 2, the binding of ([$^3$H]CPX) is reduced. A binding constant ($K_i$) is then calculated from the $IC_{50}$ according to a method by Cheng and Prusoff (Cheng and Prusoff, Biochem. Pharmacol, 22:3099 (1973), the contents of which are hereby incorporated by reference. Thus, $K_i=IC50/(1+[C^*]/K_d^*)$, where [$C^*$] is the concentration of radioligand and $K_d^*$ is its dissociation constant. The partial agonists of the invention had $K_i$ that ranged between 1 and 3 uM but preferably were less than or equal to 1 uM.

The methods of the present invention provides a means to identify compounds that are potent, partial A1 receptor agonists, that exert therapeutic effects with few to no adverse side effects. Thus, the efficacy of putative partial agonists, that is their ability to stimulate [$^{35}$S]GTPγS binding to G proteins is evaluated. A general observation is that that drugs with partial activity compared to a fall agonist such as CPA, may also behave as partial agonists for physiological parameters, such as AV nodal conduction in the heart. Then, the binding affinity of the compound is determined. The binding affinity is related to the potency of the drugs. Compounds with activity as partial agonists and a low $K_I$, (i.e., high affinity), as determined by affinity binding assays will produce drugs having the desired activity in a specific tissue at low concentrations.

The compounds identified by this invention are believed to have therapeutically useful affinities for the adenosine A1 receptor but they will have a range of intrinsic efficacies from full agonist to partial agonist. That is, some compounds may have no effect with respect to a given effector system in a given cell type, but be a full agonist in another cell type and/or effector system.

The reason for such variable pharmacological behavior relates to the magnitude of the receptor reserve for the adenosine A1 receptor in any given cell type (eg. AV nodal cells vs. adipocytes) and for a given response. The receptor reserve (spare receptor capacity) is the total number of receptors minus the fraction of receptors that is required to induce the maximal response using a full agonist. Therefore, the agonist could be a full agonist a first eliciting a response, and a partial agonist for eliciting a second response in other tissue or cells and still be an antagonist or lack activity for a third response in another tissue or cell. Consequently, a partial agonist targeted to a selected target is likely to cause fewer side effects than a full agonist. As a corollary, a full agonist elicits all the effects mediated by the respective receptor, whereas this is not necessarily the case of a partial agonist. The compounds of this invention based on their affinity for the $A_1$ receptor and their potency and selectivity to elicit $A_1$ receptor mediated responses have the potential for therapeutic intervention in the multiple disease states described above.

Partial $A_1$ agonists may have an added benefit for chronic therapy because they will be less likely to induce desensitization of the $A_1$ receptor and to cause side effects. Chronic administration of a full agonist (R-N6-phenylisopropyladenosine, R-PIA) for 7 days led to a desensitization of the A1 receptor in terms of the dromotropic response in guinea pigs (note: a decrease in receptor number was observed—D. M. Dennis, J. C. Shryock, L. Belardinelli JPET, Vol. 272 (1995) p. 1024–1035). The $A_1$ agonist induced inhibitory effect on the production of cAMP by adenylate cyclase in adipocytes has been shown to desensitize upon chronic treatment with an $A_1$ agonist as well.

This invention also provides a method of treating arrhythmias comprising administering at least one compound that is a partial adenosine receptor A1 agonist to a mammal in need of such treatment. While any partial adenosine A1 receptor will be effective preferably the partial agonist will be one identifed by the methods of the present invention.

This invention provides a method of treating arrhythmias comprising administering heterocyclic adenosine derivatives having the Formula I:

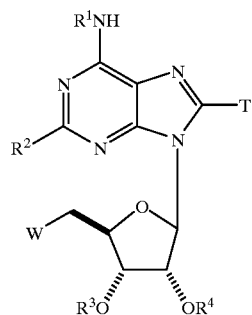

wherein
T=H or X—R⁶ and W=R⁵O or X—R⁵ or X—(C═Y)ZR⁵
X=O, S, SO, SO₂, or NR⁶
Y=O, S, N—CN, NOR⁷; and
wherein
Z=O, S, NR⁸;

R¹ is a monocyclic or polycyclic heterocyclic group containing from 3 to 15 carbon atoms wherein at least one carbon atom is replaced with an atom or molecule selected from the group consisting of N, O, P and S—(O)₀₋₂ and wherein R¹ does not contain an epoxide group;

R² is selected from the group consisting of hydrogen, halo, CF₃, and cyano;

R³, R⁴, and R⁵ are independently selected from the group consisting of hydrogen, —(CO)—R', —(CO)—R", and —(CO)—R'" wherein R', R", and R'" are independently selected from the group consisting of C₁₋₁₅ alkyl, C₂₋₁₅ alkenyl, C₂₋₁₅ alkynyl, heterocyclyl, aryl, and heteroaryl, which alkyl, alkenyl, alkynyl, aryl, heterocyclyl, and heteroaryl are optionally substituted with 1 to 3 substituents independently selected from the group of halo, NO₂, alkyl, heterocyclyl, aryl, heteroaryl, CF₃, CN, OR²⁰, SR²⁰, S(O)R²², SO₂R²², SO₂N(R²⁰)₂, SO₂NR²⁰COR²², SO₂NR²⁰CO₂R²², SO₂NR²⁰CON(R²⁰)₂, NR²⁰COR²², NR²⁰CO₂R²², NR²⁰CON(R²⁰)₂, NR²⁰C(NR²⁰)NHR²³, COR²⁰, CO₂R²⁰, CON(R²⁰)₂, CONR²⁰SO₂R²², NR²⁰SO₂R²², SO₂NR²⁰CO₂CR²², OCONR²⁰SO₂R²², OC(O)R²⁰, C(O)OCH₂OC(O)R²⁰, and OCON(R²⁰)₂ and wherein each optional heteroaryl, aryl, alkyl, and heterocyclyl substituent is optionally further substituted with halo, NO₂, alkyl, CF₃, amino, mono- or di-alkylamino, alkyl or aryl or heteroaryl amide, NR²⁰COR²², NR²⁰SO₂R²², COR²⁰, CO₂R²⁰, CON(R²⁰)₂, NR²⁰CON(R²⁰)₂, OC(O)R²⁰, OC(O)N(R²⁰)₂, SR²⁰, S(O)R²², SO₂R²², SO₂N(R²⁰)₂, CN, or OR²⁰;

R⁶ and R⁷ are independently selected from the group consisting of hydrogen, C₁₋₁₅ alkyl, C₂₋₁₅ alkenyl, C₂₋₁₅ alkynyl, heterocyclyl, aryl, and heteroaryl, wherein the alkyl, alkenyl, alkynyl, aryl, heterocyclyl and heteroaryl substituents are optionally substituted with from 1 to 3 substituents independently selected from the group consisting of halo, alkyl, NO₂, heterocyclyl, aryl, heteroaryl, CF₃, CN, OR²⁰, SR²⁰, N(R²⁰)₂, S(O)R²², SO₂R²², SO₂N(R²⁰)₂, SO₂NR²⁰COR²², SO₂NR²⁰CO₂R²², S(O)₃R²⁰, P(O)(OR²⁰)₂, SO₂NR²⁰CON(R²⁰)₂, NR²⁰COR²², NR²⁰CO₂R²², NR²⁰CON(R²⁰)₂, NR²⁰C(NR²⁰)NHR²³, COR²⁰, CO₂R²⁰, CON(R²⁰)₂, CONR²⁰SO₂R²², NR²⁰SO₂R²², SO₂NR²⁰CO₂R²², OCONR²⁰SO₂R²², OC(O)R²⁰, C(O)OCH₂OC(O)R²⁰, and OCON(R²⁰)₂ and wherein each optional heteroaryl, aryl, and heterocyclyl substituent is optionally further substituted with halo, NO₂, alkyl, CF₃, amino, mono- or di-alkylamino, alkyl or aryl or heteroaryl amide, NR²⁰COR²², NR²⁰SO₂R²², COR²⁰, CO₂R²⁰, CON(R²⁰)₂, NR²⁰CON(R²⁰)₂, OC(O)R²⁰, OC(O)N(R²⁰)₂, SR²⁰, S(O)₃R²⁰, P(O)(OR²⁰)₂, S(O)R²², SO₂R²², SO₂N(R²⁰)₂, CN, or OR²⁰.

R⁸ is selected from the group consisting of H, and C1–C3 alkyl.

R²⁰ is selected from the group consisting of H, C₁₋₁₅ alkyl, C₂₋₁₅ alkenyl, C₂₋₁₅ alkynyl, heterocyclyl, aryl, and heteroaryl, wherein the alkyl, alkenyl, alkynyl, heterocyclyl, aryl, and heteroaryl substituents are optionally substituted with from 1 to 3 substituents independently selected from halo, alkyl, mono- or dialkylamino, alkyl or aryl or heteroaryl amide, CN, O—C₁₋₆ alkyl, CF₃, aryl, and heteroaryl; and R²² is selected from the group consisting of hydrogen, C₁₋₁₅ alkyl, C₂₋₁₅ alkenyl, C₂₋₁₅ alkynyl, heterocyclyl, aryl, and heteroaryl, wherein the alkyl, alkenyl, alkynyl, heterocyclyl, aryl, and heteroaryl substituents are optionally substituted with from 1 to 3 substituents independently selected from halo, alkyl, mono- or dialkylamino, alkyl or aryl or heteroaryl amide, CN, O—C₁₋₆ alkyl, CF₃, aryl, and heteroaryl, wherein when Z=NR⁸ or when X¹=NR⁶ then R⁶ and R⁸ may bond to form a 4 or 5 or 6 membered saturated or unsaturated ring and when X¹=NR⁶ and Y=O, then R⁵ and R⁶ may bond to form a 5 membered ring wherein R⁵ and R⁶ together form C═C.

A class of partial agonists particularly useful in this invention are heterocyclic 5' modified adenosine derivatives having the formula II below:

Formula II

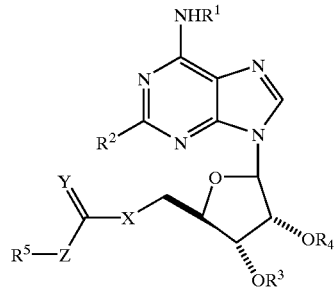

wherein
X=O, S, NR⁶; Y=O, S, N—CN, N—OR⁷; Z=O, S, NR⁸;

R¹ is a monocyclic or polycyclic heterocyclic group containing from 3 to 15 atoms, at least one of which is selected from the group consisting of N, O, P and S—(O)₀₋₂ and wherein R¹ does not contain an epoxide group;

R² is selected from the group consisting of hydrogen, halo, CF₃, and cyano;

R³ and R⁴ are each independently selected from the group consisting of hydrogen, and —(CO)—R' and —(CO)—R" wherein R', and R" are independently selected from the group consisting of C₁₋₁₅ alkyl, C₂₋₁₅ alkenyl, C₂₋₁₅ alkynyl, heterocyclyl, aryl, and heteroaryl, which alkyl, alkenyl, alkynyl, aryl, heterocyclyl, and heteroaryl are optionally substituted with 1 to 3 substituents independently selected from the group of halo, NO₂, heterocyclyl, aryl, heteroaryl, CF₃, CN, OR²⁰, SR²⁰, N(R²⁰)₂, S(O)R²², SO₂R²², SO₂N(²⁰)₂, SO₂NR²⁰CO₂R²², SO₂NR²⁰CON(R²⁰)₂, NR²⁰COR²², NR²⁰CO₂R²², NR²⁰CON(R²⁰)₂, NR²⁰C(NR²⁰)NHR²³, COR²⁰, CO₂R²⁰, CON(R²⁰)₂, CONR²⁰SO₂R²², NR²⁰SO₂R²², SO₂NR²⁰CO₂R²², OCONR²⁰SO₂R²², OC(O)R²⁰, C(O)OCH₂OC(O)R²⁰, and OCON(R²⁰)₂ and each optional heteroaryl, aryl, and heterocyclyl substituent is further optionally substituted with halo, NO₂, alkyl, CF₃, amino, mono- or di-alkylamino, alkyl or aryl or heteroaryl amide, NCOR²², NR²⁰SO₂R²², COR²⁰, CO₂R²⁰, CON(R²⁰)₂, NR²⁰CON(R²⁰)₂, OC(O)R²⁰, OC(O)N(R²⁰)₂, SR²⁰, S(O)R²², SO₂R²², SO₂N(R²⁰)₂, CN, or OR²⁰;

R⁵ is selected from the group consisting of C₁₋₁₅ alkyl, C₂₋₁₅ alkenyl, C₂₋₁₅ alkynyl, heterocyclyl, aryl, and heteroaryl, which alkyl, alkenyl, alkynyl, aryl, heterocyclyl and heteroaryl are optionally substituted with from 1 to 3 substituents independently selected from the group consisting of halo, alkyl, NO₂, heterocyclyl, aryl, heteroaryl, CF₃, CN, OR²⁰, SR²⁰, N(R²⁰)₂, S(O)R²², SO₂R²², SO₂N(R²⁰)₂, S(O)₃R²⁰, P(O)(OR²⁰)₂, SO₂NR²⁰COR²², SO₂NR²⁰CO₂R²², SO₂NR²⁰CON(R²⁰)₂, NR²⁰COR²², NR²⁰CO₂R²², NR²⁰CON(R²⁰)₂, NR²⁰C(NR²⁰)NHR²³, COR²⁰, CO₂R²⁰, CON(R²⁰)₂, CONR²⁰SO₂R²², NR²⁰SO₂R²², SO₂NR²⁰CO₂R²², OCONR²⁰SO₂R²², OC(O)R²⁰, C(O)OCH₂OC(O)R²⁰, and OCON(R²⁰)₂ and each optional alkyl, heteroaryl, aryl, and heterocyclyl substituent is further optionally substituted with halo, NO₂, alkyl, CF₃, amino, mono- or di-alkylamino, alkyl or aryl or heteroaryl amide, NCOR²², NR²⁰SO₂R²², COR²⁰, CO₂R²⁰)₂, CON(R²⁰)₂, NR²⁰CON(R²⁰)₂, OC(O)R²⁰, OC(O)N(R²⁰)₂, S(O)₃R²⁰, P(O)(OR²⁰)₂, SR²⁰, S(O)R²², SO₂R²², SO₂N(R²⁰)₂, CN, or OR²⁰;

R⁶ is selected from the group consisting of H, C₁₋₆ alkyl and aryl optionally substituted with halo, CN, CF₃, OR²⁰ and N(R²⁰)₂, with the proviso that when Z=NR⁸ then R⁶ and R⁸ may bond to form a 5 or 6 membered saturated or unsaturated ring;

R⁷ and R⁸ are independently selected from the group consisting of H, and C₁–C₁₅ alkyl optionally substituted with one aryl substituent that is optionally substituted with halo or CF₃;

R²⁰ is selected from the group consisting of H, C₁₋₁₅ alkyl, C₂₋₁₅ alkenyl, C₂₋₁₅ alkynyl, heterocyclyl, aryl, and heteroaryl, wherein the alkyl, alkenyl, alkynyl, heterocyclyl, aryl, and heteroaryl substituents are optionally substituted with from 1 to 3 substituents independently selected from halo, alkyl, mono- or dialkylamino, alkyl or aryl or heteroaryl amide, CN, O—C₁₋₆ alkyl, CF₃, aryl, and heteroaryl; and R²² is selected from the group consisting of hydrogen, C₁₋₁₅ alkyl, C₂₋₁₅ alkenyl, C₂₋₁₅ alkynyl, heterocyclyl, aryl, and heteroaryl, wherein the alkyl, alkenyl, alkynyl, heterocyclyl, aryl, and heteroaryl substituents are optionally substituted with from 1 to 3 substituents independently selected from halo, alkyl, mono- or dialkylamino, alkyl or aryl or heteroaryl amide, CN, O—C₁₋₆ alkyl, CF₃, aryl, and heteroaryl, wherein when Z=NR⁸ or when X=NR⁶ then R⁵ and R⁸ may bond to form a 4 or 5 or 6 membered saturated or unsaturated ring and when X=NR⁶ and Y=O, then R⁵ and R⁶ may bond to form a 5 membered ring wherein R⁵ and R⁶ together form C=C.

A most preferred compound of the invention has the formula III below:

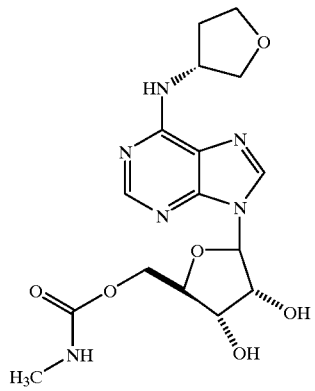

Hereafter referred to as (5-[6-[((3R)oxolan-3-yl)amino]purin-9-yl](3S,2R,4R,5R)-3,4,-dihydroxyoxolanyl)methoxy]-N-methylcarboxamide or as CVT-2759.

The following definitions apply to terms as used herein.

"Halo" or "Halogen"—alone or in combination means all halogens, that is, chloro (Cl), fluoro (F), bromo (Br), iodo (I).

"Hydroxyl" refers to the group —OH.

"Thiol" or "mercapto" refers to the group —SH.

"Alkyl"—alone or in combination means an alkane-derived radical containing from 1 to 20, preferably 1 to 15, carbon atoms (unless specifically defined). It is a straight chain alkyl, branched alkyl or cycloalkyl. Preferably, straight or branched alkyl groups containing from 1–15, more preferably 1 to 8, even more preferably 1–6, yet more preferably 1–4 and most preferably 1–2, carbon atoms, such as methyl, ethyl, propyl, isopropyl, butyl, t-butyl and the like. The term "lower alkyl" is used herein to describe the straight chain alkyl groups described immediately above. Preferably, cycloalkyl groups are monocyclic, bicyclic or tricyclic ring systems of 3–8, more preferably 3–6, ring members per ring, such as cyclopropyl, cyclopentyl, cyclohexyl, adamantyl and the like. Alkyl also includes a straight chain or branched alkyl group that contains or is interrupted by a cycloalkyl portion. The straight chain or branched alkyl group is attached at any available point to produce a stable compound. Examples of this include, but are not limited to, 4-(isopropyl)-cyclohexylethyl or 2-methyl-cyclopropylpentyl. A substituted alkyl is a straight chain alkyl, branched alkyl, or cycloalkyl group defined previously, independently substituted with 1 to 3 groups or substituents of halo, hydroxy, alkoxy, alkylthio, alkylsulfinyl, alkylsulfonyl, acyloxy, aryloxy, heteroaryloxy, amino optionally mono- or di-substituted with alkyl, aryl or heteroaryl groups, amidino, urea optionally substituted with alkyl, aryl, heteroaryl or heterocyclyl groups, aminosulfonyl optionally N-mono- or N,N-di-substituted with alkyl, aryl or heteroaryl groups, alkylsulfonylamino, arylsulfonylamino, heteroarylsulfonylamino, alkylcarbonylamino, arylcarbonylamino, heteroarylcarbonylamino, or the like.

"Alkenyl"—alone or in combination means a straight, branched, or cyclic hydrocarbon containing 2–20, preferably 2–17, more preferably 2–10, even more preferably 2–8, most preferably 2–4, carbon atoms and at least one, preferably 1–3, more preferably 1–2, most preferably one, carbon to carbon double bond. In the case of a cycloalkyl group, conjugation of more than one carbon to carbon double bond is not such as to confer aromaticity to the ring. Carbon to carbon double bonds may be either contained within a cycloalkyl portion, with the exception of cyclopropyl, or within a straight chain or branched portion. Examples of alkenyl groups include ethenyl, propenyl, isopropenyl, butenyl, cyclohexenyl, cyclohexenylalkyl and the like. A substituted alkenyl is the straight chain alkenyl, branched alkenyl or cycloalkenyl group defined previously, independently substituted with 1 to 3 groups or substituents of halo, hydroxy, alkoxy, alkylthio, alkylsulfinyl, alkylsulfonyl, acyloxy, aryloxy, heteroaryloxy, amino optionally mono- or di-substituted with alkyl, aryl or heteroaryl groups, amidino, urea optionally substituted with alkyl, aryl, heteroaryl or heterocyclyl groups, aminosulfonyl optionally N-mono- or N,N-di-substituted with alkyl, aryl or heteroaryl groups, alkylsulfonylamino, arylsulfonylamino, heteroarylsulfonylamino, alkylcarbonylamino, arylcarbonylamino, heteroarylcarbonylamino, carboxy, alkoxycarbonyl, aryloxycarbonyl, heteroaryloxycarbonyl, or the like attached at any available point to produce a stable compound.

"Alkynyl"—alone or in combination means a straight or branched hydrocarbon containing 2–20, preferably 2–17, more preferably 2–10, even more preferably 2–8, most preferably 2–4, carbon atoms containing at least one, preferably one, carbon to carbon triple bond. Examples of alkynyl groups include ethynyl, propynyl, butynyl and the like. A substituted alkynyl refers to the straight chain alkynyl or branched alkenyl defined previously, independently substituted with 1 to 3 groups or substituents of halo, hydroxy, alkoxy, alkylthio, alkylsulfinyl, alkylsulfonyl, acyloxy, aryloxy, heteroaryloxy, amino optionally mono- or di-substituted with alkyl, aryl or heteroaryl groups, amidino, urea optionally substituted with alkyl, aryl, heteroaryl or heterocyclyl groups, aminosulfonyl optionally N-mono- or N,N-di-substituted with alkyl, aryl or heteroaryl groups, alkylsulfonylamino, arylsulfonylamino, heteroarylsulfonylamino, alkylcarbonylamino, arylcarbonylamino, heteroarylcarbonylamino, or the like attached at any available point to produce a stable compound.

"Alkyl alkenyl" refers to a group —R—CR'=CR'"R"", where R is lower alkyl, or substituted lower alkyl, R', R'", R"" may independently be hydrogen, halogen, lower alkyl, substituted lower alkyl, acyl, aryl, substituted aryl, hetaryl, or substituted hetaryl as defined below.

"Alkyl alkynyl" refers to a groups —RC≡CR' where R is lower alkyl or substituted lower alkyl, R' is hydrogen, lower alkyl, substituted lower alkyl, acyl, aryl, substituted aryl, hetaryl, or substituted hetaryl as defined below.

"Alkoxy" denotes the group —OR, where R is lower alkyl, substituted lower alkyl, acyl, aryl, substituted aryl, aralkyl, substituted aralkyl, heteroalkyl, heteroarylalkyl, cycloalkyl, substituted cycloalkyl, cycloheteroalkyl, or substituted cycloheteroalkyl as defined.

"Alkylthio" denotes the group —SR, —S(O)$_{n=1-2}$—R, where R is lower alkyl, substituted lower alkyl, aryl, substituted aryl, aralkyl or substituted aralkyl as defined herein.

"Acyl" denotes groups —C(O)R, where R is hydrogen, lower alkyl substituted lower alkyl, aryl, substituted aryl and the like as defined herein.

"Aryloxy" denotes groups —OAr, where Ar is an aryl, substituted aryl, heteroaryl, or substituted heteroaryl group as defined herein.

"Amino" denotes the group NRR', where R and R' may independently by hydrogen, lower alkyl, substituted lower alkyl, aryl, substituted aryl, hetaryl, or substituted hetaryl as defined herein or acyl.

"Amido" denotes the group —C(O)NRR', where R and R' may independently by hydrogen, lower alkyl, substituted lower alkyl, aryl, substituted aryl, hetaryl, substituted hetaryl as defined herein.

"Carboxyl" denotes the group —C(O)OR, where R is hydrogen, lower alkyl, substituted lower alkyl, aryl, substituted aryl, hetaryl, and substituted hetaryl as defined herein.

"Aryl"—alone or in combination means phenyl or naphthyl optionally carbocyclic fused with a cycloalkyl of preferably 5–7, more preferably 5–6, ring members and/or optionally substituted with 1 to 3 groups or substituents of halo, hydroxy, alkoxy, alkylthio, alkylsulfinyl, alkylsulfonyl, acyloxy, aryloxy, heteroaryloxy, amino optionally mono- or di-substituted with alkyl, aryl or heteroaryl groups, amidino, urea optionally substituted with alkyl, aryl, heteroaryl or heterocyclyl groups, aminosulfonyl optionally N-mono- or N,N-di-substituted with alkyl, aryl or heteroaryl groups, alkylsulfonylamino, arylsulfonylamino, heteroarylsulfonylamino, alkylcarbonylamino, arylcarbonylamino, heteroarylcarbonylamino, or the like.

"Substituted aryl" refers to aryl optionally substituted with one or more functional groups, e.g., halogen, lower alkyl, lower alkoxy, alkylthio, acetylene, amino, amido, carboxyl, hydroxyl, aryl, aryloxy, heterocycle, hetaryl, substituted hetaryl, nitro, cyano, thiol, sulfamido and the like.

"Heterocycle" refers to a saturated, unsaturated, or aromatic carbocyclic group having a single ring (e.g., morpholino, pyridyl or furyl) or multiple condensed rings (e.g., naphthpyridyl, quinoxalyl, quinolinyl, indolizinyl or benzo[b]thienyl) and having at least one hetero atom, such as N, O or S, within the ring, which can optionally be unsubstituted or substituted with, e.g., halogen, lower alkyl, lower alkoxy, alkylthio, acetylene, amino, amido, carboxyl, hydroxyl, aryl, aryloxy, heterocycle, hetaryl, substituted hetaryl, nitro, cyano, thiol, sulfamido and the like.

"Heteroaryl"—alone or in combination means a monocyclic aromatic ring structure containing 5 or 6 ring atoms, or a bicyclic aromatic group having 8 to 10 atoms, containing one or more, preferably 1–4, more preferably 1–3, even more preferably 1–2, heteroatoms independently selected from the group O, S, and N, and optionally substituted with 1 to 3 groups or substituents of halo, hydroxy, alkoxy, alkylthio, alkylsulfinyl, alkylsulfonyl, acyloxy, aryloxy, heteroaryloxy, amino optionally mono- or di-substituted with alkyl, aryl or heteroaryl groups, amidino, urea optionally substituted with alkyl, aryl, heteroaryl or heterocyclyl groups, aminosulfonyl optionally N-mono- or N,N-di-substituted with alkyl, aryl or heteroaryl groups, alkylsulfonylamino, arylsulfonylamino, heteroarylsulfonylamino, alkylcarbonylamino, arylcarbonylamino, heteroarylcarbonylamino, or the like. Heteroaryl is also intended to include oxidized S or N, such as sulfinyl, sulfonyl and N-oxide of a tertiary ring nitrogen. A carbon or nitrogen atom is the point of attachment of the heteroaryl ring structure such that a stable aromatic ring is retained. Examples of heteroaryl groups are pyridinyl, pyridazinyl, pyrazinyl, quinazolinyl, purinyl, indolyl, quinolinyl, pyrimidinyl, pyrrolyl, oxazolyl, thiazolyl, thienyl, isoxazolyl, oxathiadiazolyl, isothiazolyl, tetrazolyl, imidazolyl, triazinyl, furanyl, benzofuryl, indolyl and the like. A substituted heteroaryl contains a substituent attached at an available carbon or nitrogen to produce a stable compound.

"Heterocyclyl"—alone or in combination means a non-aromatic cycloalkyl group having from 5 to 10 atoms in which from 1 to 3 carbon atoms in the ring are replaced by heteroatoms of O, S or N, and are optionally benzo fused or fused heteroaryl of 5–6 ring members and/or are optionally substituted as in the case of cycloalkyl. Heterocyyl is also intended to include oxidized S or N, such as sulfinyl, sulfonyl and N-oxide of a tertiary ring nitrogen. The point of attachment is at a carbon or nitrogen atom. Examples of heterocyclyl groups are tetrahydrofuranyl, dihydropyridinyl, piperidinyl, pyrrolidinyl, piperazinyl, dihydrobenzofuryl, dihydroindolyl, and the like. A substituted hetercyclyl contains a substituent nitrogen attached at an available carbon or nitrogen to produce a stable compound.

"Substituted heteroaryl" refers to a heterocycle optionally mono or poly substituted with one or more functional groups, e.g., halogen, lower alkyl, lower alkoxy, alkylthio, acetylene, amino, amido, carboxyl, hydroxyl, aryl, aryloxy, heterocycle, substituted heterocycle, hetaryl, substituted hetaryl, nitro, cyano, thiol, sulfamido and the like.

"Aralkyl" refers to the group —R—Ar where Ar is an aryl group and R is lower alkyl or substituted lower alkyl group. Aryl groups can optionally be unsubstituted or substituted with, e.g., halogen, lower alkyl, alkoxy, alkylthio, acetylene, amino, amido, carboxyl, hydroxyl, aryl, aryloxy, heterocycle, substituted heterocycle, hetaryl, substituted hetaryl, nitro, cyano, thiol, sulfamido and the like.

"Heteroalkyl" refers to the group —R-Het where Het is a heterocycle group and R is a lower alkyl group. Heteroalkyl groups can optionally be unsubstituted or substituted with e.g., halogen, lower alkyl, lower alkoxy, alkylthio, acetylene, amino, amido, carboxyl, aryl, aryloxy, heterocycle, substituted heterocycle, hetaryl, substituted hetaryl, nitro, cyano, thiol, sulfamido and the like.

"Heteroarylalkyl" refers to the group —R-HetAr where HetAr is an heteroaryl group and R lower alkyl or substituted lower alkyl. Heteroarylalkyl groups can optionally be unsubstituted or substituted with, e.g., halogen, lower alkyl, substituted lower alkyl, alkoxy, alkylthio, acetylene, aryl, aryloxy, heterocycle, substituted heterocycle, hetaryl, substituted hetaryl, nitro, cyano, thiol, sulfamido and the like.

"Cycloalkyl" refers to a divalent cyclic or polycyclic alkyl group containing 3 to 15 carbon atoms.

"Substituted cycloalkyl" refers to a cycloalkyl group comprising one or more substituents with, e.g., halogen, lower alkyl, substituted lower alkyl, alkoxy, alkylthio, acetylene, aryl, aryloxy, heterocycle, substituted heterocycle, hetaryl, substituted hetaryl, nitro, cyano, thiol, sulfamido and the like.

"Cycloheteroalkyl" refers to a cycloalkyl group wherein one or more of the ring carbon atoms is replaced with a heteroatom (e.g., N, O, S or P).

"Substituted cycloheteroalkyl" refers to a cycloheteroalkyl group as herein defined which contains one or more substituents, such as halogen, lower alkyl, lower alkoxy, alkylthio, acetylene, amino, amido, carboxyl, hydroxyl, aryl, aryloxy, heterocycle, substituted heterocycle, hetaryl, substituted hetaryl, nitro, cyano, thiol, sulfamido and the like.

"Alkyl cycloalkyl" denotes the group —R-cycloalkyl where cycloalkyl is a cycloalkyl group and R is a lower alkyl or substituted lower alkyl. Cycloalkyl groups can optionally be unsubstituted or substituted with e.g. halogen, lower alkyl, lower alkoxy, alkylthio, acetylene, amino, amido, carboxyl, hydroxyl, aryl, aryloxy, heterocycle, substituted heterocycle, hetaryl, substituted hetaryl, nitro, cyano, thiol, sulfamido and the like.

"Alkyl cycloheteroalkyl" denotes the group —R-cycloheteroalkyl where R is a lower alkyl or substituted lower alkyl. Cycloheteroalkyl groups can optionally be unsubstituted or substituted with e.g. halogen, lower alkyl, lower alkoxy, alkylthio, amino, amido, carboxyl, acetylene, hydroxyl, aryl, aryloxy, heterocycle, substituted heterocycle, hetaryl, substituted hetaryl, nitro, cyano, thiol, sulfamido and the like.

The compounds above can be prepared as described in U.S. Pat. No. 5,789,416, and U.S. patent application Ser. No. 09/454,485, now U.S. Pat. No. 6,294,522, Ser. No. 09/454,436, now U.S. Pat. No. 6,258,793 and Ser. No. 09/454,136, the patent specifications of which are incorporated herein by reference. The pro-compound esters of this invention can be prepared using all of the known methods for ester formation which are included by reference (see Jerry March Organic synthesis and Richard Larock—Methods of Organic Synthesis), and more preferably by those outlined in this application.

This invention also includes pro-compounds of the above-identified $A_1$ agonists. A pro-compound is a compound which has been chemically modified and may be biological inactive at its site of action, but which will be degraded or modified by one or more enzymatic or in vivo processes to the bioactive form. The pro-compounds of this invention should have a different pharmacokinetic profile to the parent enabling improved absorption across the mucosal epithelium, better salt formulation and/or solubility and improved systemic stability. The above-identified compounds may be preferably modified at one or more of the hydroxyl groups. The modifications may be (1) ester or carbamate derivatives which may be cleaved by esterases or lipases, for example; (2) peptides which may be recognized by specific or non specific proteinase; or (3) derivatives that accumulate at a site of action through membrane selection or a pro-compound form or modified pro-compound form, or any combination of (1) to (3) above.

If the final compound of this invention contains a basic group, an acid addition salt may be prepared. Acid addition salts of the compounds are prepared in a standard manner in a suitable solvent from the parent compound and an excess of acid, such as hydrochloric, hydrobromic, sulfuric, phosphoric, acetic, maleic, succinic, or methanesulfonic. The hydrochloric salt form is especially useful. If the final compound contains an acidic group, cationic salts may be prepared. Typically the parent compound is treated with an excess of an alkaline reagent, such as hydroxide, carbonate or alkoxide, containing the appropriate cation. Cations such as $Na^+$, $K^+$, $Ca^{+2}$ and $NH_4^+$ are examples of cations present in pharmaceutically acceptable salts. Certain of the compounds form inner salts or zwitterions which may also be acceptable.

This invention also includes pro-compounds of the $A_1$ agonist compositions of this invention. A pro-compound is a compound which has been chemically modified and may be biologically inactive at its site of action, but which will be degraded or modified by one or more enzymatic or in vivo processes to the bioactive form. The pro-compounds of this invention should have a different pharmacokinetic profile to the parent enabling improved absorption across the mucosal epithelium, better salt formulation and/or solubility and improved systemic stability. The compounds of this invention may be preferably modified at one or more of the hydroxyl groups to form pro-compounds. The modifications may be (1) ester or carbamate derivatives which may be cleaved by esterases or lipases, for example; (2) peptides which may be recognized by specific or non specific proteinase; or (3) derivatives that accumulate at a site of action through membrane selection or a pro-compound form or modified pro-compound form, or any combination of (1) to (3) above.

If a compound of this invention contains a basic group, then corresponding acid addition salt may be prepared. Acid addition salts of the compounds are prepared in a standard manner in a suitable solvent from the parent compound and an excess of acid, such as hydrochloric, hydrobromic, sulfuric, phosphoric, acetic, maleic, succinic, or methanesulfonic. The hydrochloric salt form is especially useful. If a compound of this invention contains an acidic group, then corresponding cationic salts may be prepared. Typically the parent compound is treated with an excess of an alkaline reagent, such as hydroxide, carbonate or alkoxide, containing the appropriate cation. Cations such as $Na^+$, $K^+$, $Ca^{+2}$ and $NH_4^+$ are examples of cations present in pharmaceutically acceptable salts. Certain of the compounds form inner salts or zwitterions which may also be acceptable.

The compositions of this invention are useful for treating a variety of mammalian disorders and preferably human disorders that are mediated by an Adenosine A1 receptor. For example, the compositions of this invention are useful for modifying cardiac activity in mammals experiencing a coronary electrical disorder that can be treated by stimulating an Adenosine A1 receptor. Examples of coronary electrical disorders that can be treated by the compositions of this invention include supraventricular tachycardias, atrial fibrillation, atrial flutter, and AV nodal re-entrant tachycardia. Furthermore, orally active A1 agonists of this invention that demonstrate an excellent safety profile in treating supraventricular arrhythmias may also be used as a prophylactic for those at high risk of a myocardial ischemia.

The compositions of this invention are further useful for providing cardiomyocyte protection from ischemic events by stimulating an Adenosine A1 receptor. Ischemic events treatable using the compositions of this invention include stable angina, unstable angina, cardiac transplant, and myocardial infarction.

The compositions of this invention may be administered orally, intravenously, through the epidermis, bolus, nasally, by inhalation or by any other means known in the art for administering a therapeutic agents. The method of treatment comprises the administration of an effective quantity of the chosen compound, preferably dispersed in a pharmaceutical carrier. Dosage units of the active ingredient are generally selected from the range of 0.01 to 100 mg/kg, but will be readily determined by one skilled in the art depending upon the route of administration, age and condition of the patient.

Pharmaceutical compositions including the compounds of this invention, and/or derivatives thereof, may be formulated as solutions or lyophilized powders for parenteral administration. Powders may be reconstituted by addition of a suitable diluent or other pharmaceutically acceptable carrier prior to use. If used in liquid form the compositions of this invention are preferably incorporated into a buffered, isotonic, aqueous solution. Examples of suitable diluents are normal isotonic saline solution, standard 5% dextrose in water and buffered sodium or ammonium acetate solution. Such liquid formulations are suitable for parenteral administration, but may also be used for oral administration. It may be desirable to add excipients such as polyvinylpyrrolidinone, gelatin, hydroxycellulose, acacia, polyethylene glycol, mannitol, sodium chloride, sodium citrate or any other excipient known to one of skill in the art to pharmaceutical compositions including compounds of this invention. Alternatively, the pharmaceutical compounds may be encapsulated, tableted or prepared in an emulsion or syrup for oral administration. Pharmaceutically acceptable solid or liquid carriers may be added to enhance or stabilize the composition, or to facilitate preparation of the composition. Liquid carriers include syrup, peanut oil, olive oil, glycerin, saline, alcohols and water. Solid carriers include starch, lactose, calcium sulfate, dihydrate, teffa alba, magnesium stearate or stearic acid, talc, pectin, acacia, agar or gelatin. The carrier may also include a sustained release material such as glycerol monostearate or glycerol distearate, alone or with a wax. The amount of solid carrier varies but, preferably, will be between about 20 mg to about 1 gram per dosage unit. The pharmaceutical dosages are made using conventional techniques such as milling, mixing, granulation, and compressing, when necessary, for tablet forms; or milling, mixing and filling for hard gelatin capsule forms. When a liquid carrier is used, the preparation will be in the form of a syrup, elixir, emulsion or an aqueous or non-aqueous suspension. Such a liquid formulation may be administered directly or filled into a soft gelatin capsule.

The Examples which follow serve to illustrate this invention. The Examples are intended to in no way limit the scope of this invention, but are provided to show how to make and use the compounds of this invention.

EXAMPLES

Example 1

The following examples are biological assays used to evaluate compounds prepared in Examples 2–4 below.

Reagents: The $A_1$-AdoR antagonists 8-cyclopentyl-1,3-dipropylxanthine (CPX) and 8-cyclopentyl-1,3-dimethylxanthine (CPT), the $A_1$-AdoR agonists $N^6$-cyclopentyladenosine (CPA), 2-chloro-$N^6$-cyclopentyladenosine (CCPA), and N-cyclohexyladenosine (CHA), the adenosine deaminase inhibitor erythro-9-(2-hydroxy-3-nonyl)adenine (EHNA), the adenosine kinase inhibitor iodotubercidin, and forskolin were purchased from Research Biochemicals (Natick, Mass.). CVT-2759, [(5-{6-[((3R)oxolan-3-yl)amino]purin-9-yl}(3 S,2R,4R)-3,4-dihydroxyoxolan-2-yl)methoxy]-N-methylcarboxamide, molecular weight 394.38 was prepared as set forth in Example 2—Compound 6. Adenosine was purchased from Sigma Chemical Co. (St. Louis, Mo.). The radioligand 8-cyclopentyl-1,3-dipropyl-[2,3-$^3$H(N)]xanthine ($^3$H-CPX) was purchased from New England Nuclear (Boston, Mass.). Concentrated stock solutions (10–100 mM) of Compound 6 of Example 2, CPX, CPT, CPA, CCPA, CHA, and forskolin were dissolved in dimethylsulfoxide, stored as aliquots at −80° C., and diluted in physiological saline for use in experiments. The final content of dimethylsulfoxide in saline during experiments was not more than 0.1%. Adenosine and EHNA were dissolved in saline immediately before use. All values are reported herein as mean±SE. Concentration-response and radioligand binding data were analyzed using GraphPad Prism version 2.01 (San Diego, Calif.). When appropriate, the significance of differences among 3 or more individual mean values was determined by one-way ANOVA followed by Student-Newman-Keuls test. A P value less than 0.05 was considered to indicate a statistically significant difference.

Binding Assays:

Membranes containing $A_1$-AdoRs for use in radioligand binding assays were prepared from guinea pig cerebral cortex or from rat isolated epididymal adipocytes. Freshly-isolated guinea pig brain cortical tissue was homogenized in ice-cold 50 mM Tris-HCl buffer (pH 7.4) using six up and down strokes of an ice-chilled Potter-Elvejhem tissue grinder and a motor-driven teflon™ pestle. A crude membrane preparation was isolated by centrifugation of the homogenate at 15,000×g for 20 min at 4° C. The membrane pellet was resuspended in fresh Tris buffer and pelleted again by centrifugation. The final membrane pellet was suspended in Tris buffer to achieve a protein content of 1.1–1.4 mg/ml and divided into aliquots for storage at −80° C. until needed for assays. Adipocytes were isolated from 10 epididymal fat pads and suspended in a homogenization buffer (pH 7.3) containing 250 mM sucrose, 20 mM HEPES, 1 mM EDTA, 10 μg/ml leupeptin, and 5 μg/ml pepstatin. Cells were homogenized using an ice-chilled Potter-Elvehjem tissue grinder and a motor-driven teflon™ pestle. Cell membranes were separated from fat by centrifugation of the homogenate for 5 min at 1000×g at 4° C. The infranate below the fat cake was removed and placed in a centrifuge tube. Membranes were collected by centrifugation of the infranate for 30 min at 20,000×g at 4° C. Membranes were resuspended in buffer (pH 7.1 at room temperature) containing 154 mM NaCl, 10 mM $MgCl_2$, 50 mM HEPES, 1 mM EDTA, 5 μg/ml leupeptin, 5 μg/ml pepstatin, and 5 U/ml adenosine deaminase, and stored as aliquots in liquid nitrogen until needed for assays.

[$^{35}$S]GTPγS Binding:

$A_1$-agonist stimulated [$^{35}$S]GTPγS binding was determined by incubating membrane protein (30–50 υg) was incubated in a volume of 0.1 ml containing 50 mM Tris-HCl buffer pH 7.4, 5 mM $MgCl_2$, 100 mM NaCl, 1 mM dithiothreitol, 0.2 units ml-1 adenosine deaminase, 0.5% BSA, 1 mM EDTA, 10 mM GDP, 0.3 μM [$^{35}$S]GTPγS and with or without varying concentrations of CPA for 90 min at 30° C. Nonspecific binding was determined by the addition of 10 υM [$^{35}$S]GTPγS. Agonist stimulated binding was determined as the difference between total binding in the presence of CPA and basal binding determined in the absence of CPA. In preliminary experiments, it was found that 10 υM GDP gave the optimal stimulation of CPA dependent [$^{35}$S]GTPγS binding and this concentration was therefore used in all studies. In saturation experiments, 0.5 nM [$^{35}$S]GTPγS-was incubated with 0.5–1000 nM [$^{35}$S]GTPγS. At the end of the incubation, each suspension was filtered and the retained radioactivity determined as described above. Results are presented normalized to the full agonist N-6-cyclopentyladenosine, CPA.

Figure 1:
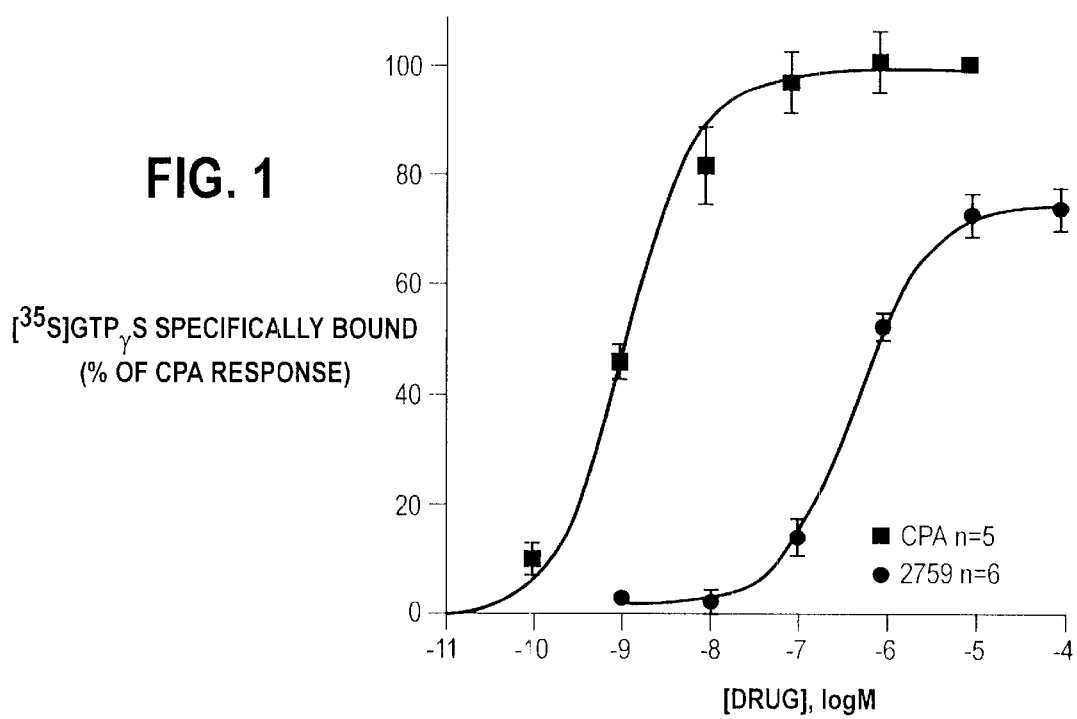
FIG. 1. Stimulation of binding of $[^{35}S]GTP\gamma S$ to G proteins by CPA and CVT-2759 (Compound 6 of Example 2). Membranes were incubated with various concentrations of CPA and Compound 6 of Example 2. Results are presented normalized to the full agonist, CPA.

A dose-response curve for a full and an experimental agonist to stimulate [$^{35}$S]GTPγS binding to G proteins is shown in FIG. 1. As shown, the experimental agonist produced a partial effect, that is, a response that was 75% of that of the full agonist.

Affinity Binding:

The binding affinity of experimental agonists high and low affinity states of the A1-ADOR was determined. Briefly, membranes were incubated with experimental agonists and a full agonist CPA in the presence or absence of GTP. The presence of GTP reduces the availability of high affinity binding sites on the GPCR. Thus, the method allows for a discrimination between high and low binding affinities.

Cell membranes (10 μg protein), $^3$H-CPX (0.5–0.8 nM), adenosine deaminase (2 U/ml), and either a putative partial agonist ($10^{-11}$ to $10^{-4}$ M) or CPA ($10^{-11}$ to $10^{-5}$ M) were incubated in a total volume of 300 μl of 50 mM Tris buffer (pH 7.4) containing N-ethylmaleimide and from 0–1 mM GTP. After a 3 hour incubation at room temperature. the reaction was terminated by diluting the samples with ice-cold Tris buffer and immediate collection of membranes onto glass-fiber filters (Schleicher and Schuell, Keene, N.H.) by vacuum filtration using a cell harvester (Brandel, Gaithersburg, Md.). Filters were washed quickly three times with ice-cold buffer to remove unbound radioligand. Filter discs containing trapped membranes and bound radioligand were placed in 4 ml of scintillation cocktail and radioactivity of samples was quantified using a liquid scintillation counter. Assays to quantitate the affinities of CPA and putative partial agonists for $A_1$-AdoRs were conducted in parallel. Six and three determinations were done at each concentration of experimental agonists and CPA, respectively. Specific binding of $^3$H-CPX was calculated as the difference between total radioligand bound and radioligand bound in the presence of the highest tested concentration of displacing ligand. Results of radioligand binding assays were analyzed using the Prism program from GraphPad (San Diego, Calif.). Values of $K_1$ were calculated from values of the $IC_{50}$ for each ligand to displace the binding of $^3$H-CPX, by use of the Cheng-Prusoff equation. Accordingly, $K_1=IC_{50}/(1+[C^*]/K_d^*)$, where [$C^*$] is the concentration of radioligand and $K_d^*$ is its dissociation constant. Values of the $K_d$ for $^3$H-CPX binding to membranes prepared from guinea pig brain and rat adipocytes were 1.4 and 0.4 nM, respectively, as determined by saturation binding assays.

A-V Nodal Conduction.

This method evaluates the potencies of compounds to cause coronary vasodilation ($A_{2A}$ AdoR response) and to prolong A-V nodal conduction time ($A_1$ AdoR response).

Materials

Sprague Dawley rats were purchased from Simonsen. Hartley guinea pigs were purchased from Charles River. Compound 18 was prepared as described above. Ketamine was purchased from Fort Dodge Animal Health (Lot No. 440444) and xylazine from Bayer (Lot No. 26051 A). Krebs-Henseleit solution was prepared according to the standard methods, and 0.9% sodium chloride was purchased from McGraw, Inc. (Lot No. J8B246).

Isolated Perfused Heart Preparation:

Rats and guinea pigs, of either sex weighing from 230 to 260 grams and 300 to 350 grams, respectively, were used in this study. Animals were anesthetized by peritoneal injection of a cocktail containing ketamine and xylazine (ketamine 100 mg, xylazine 20 mg/ml). The chest was opened and the heart quickly removed. The heart was briefly rinse in ice-cold Krebs-Henseleit solution (see below), and the aorta cannulated. The heart was then perfused at a flow rate of 10 ml/min with modified Krebs-Henseleit (K-H) solution containing NaCl 117.9, KCl 4.5, $CaCl_2$ 2.5, $MgSO_4$ 1.18, $KH_2PO_4$ 1.18, pyruvate 2.0 mmol. The K-H solution (pH 7.4) was gassed continuously with 95% $O_2$ and 5% $CO_2$ and warmed to 35±0.50° C. The heart was electrically paced at a fixed cycle length of 340 ms (250 beats/min) using a bipolar electrode place on the left atrium. The electrical stimuli were generated by a Grass stimulator (Model S48, W. Warwick, R.I.) and delivered through a Stimuli Isolation Unit (Model SIU5, Astro-Med, Inc., NY) as square-wave pulses of 3-msec in duration and amplitude of at least twice the threshold intensity.

Coronary perfusion pressure (CPP) was measured using a pressure transducer, connected to the aortic cannula via a T-connector positioned approximately 3 cm above the heart. Coronary perfusion pressure was monitored throughout the experiment and recorded either on a chart recorder (Gould Recorder 2200S) or a computerized recording system (PowerLab/4S, ADInstruments Pty Ltd, Australia). Only hearts with CPP ranging from 60 to 85 mmHg (in the absence of drugs) were used in the study. Coronary conductance (in ml/min/mmHg) was calculated as the ratio between coronary perfusion rate (10 ml/min) and coronary perfusion pressure.

$A_1$ adenosine receptor-mediated depression of A-V nodal conduction time (negative dromotropic effect) was measured. Atrial and ventricular surface electrograms in rats and His bundle electrogram in guinea pigs, were recorded during constant atrial pacing.

The effects of compounds on coronary conductance ($A_{2A}$ effect) and atrioventricular conduction time or stimulus-to- His-bundle (S-H) interval ($A_1$ effect) was then determined. Hearts were instrumented for continuous recording of coronary perfusion pressure ($A_{2A}$ response) and atrioventricular (A-V) conduction time or S-H interval ($A_1$ response). In each experiment, concentration-response relationship of compounds to increase coronary conductance and to prolong A-V conduction time or S-H interval was determined. After control measurements of CPP and A-V conduction time or S-H interval were made, progressive higher concentrations of the compound studied was administered until maximal coronary vasodilation and A-V nodal conduction time or S-H interval prolongation were achieved.

Examples 2–4 below detail methods for synthesizing partial A1 agonists as well as the results of one or more compound assays.

Example 2

Preparation of compounds 6 and 7 starting from compound 3 is shown in the synthesis scheme below. Compound 3 was prepared from 6-chloropurineriboside 1 and 3 (R)-aminotetrahydrofuran following the procedure reported earlier (U.S. Pat. No. 5,789,416). Protection of the 2' and 3' hydroxy groups as an acetonide with 2,2-dimethoxypropane in the presence of TsOH(cat.) gave 4. Reaction of 4 with CDI in THF followed by treatment with 40% aq.methylamine gave carbamate 5. Deprotection of the 2',3' acetonide with 80% AcOH/water at 80–90 C. gave carbamate 6. Esterification of 6 with acetic anhydride in pyridine gave diester 7.

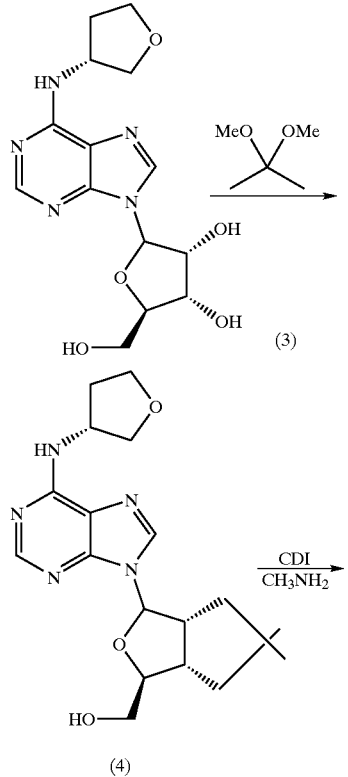

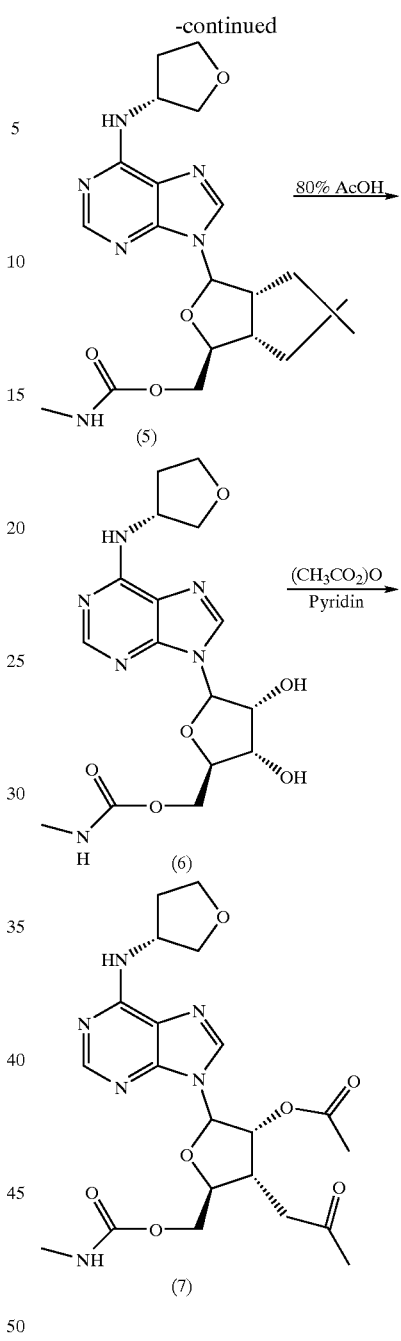

[(5-{6-[((3R)oxolan-3-yl)amino]purin-9-yl}(3S,2R,4R,5R)-3,4-dihydroxyoxolan-2-yl)methoxy]-N-ethylcarboxamide (25)

This compound was prepared in a manner similar to that of 6, substituting ethyl amine for methyl amine: (M+1)= 409.35

[(5-{6-[((3R)oxolan-3-yl)amino]purin-9-yl}(3S,2R$^4$R,5R)-3,4-dihydroxyoxolan-2-yl)methoxy]-N-propylcarboxamide (26)

This compound was prepared in a manner similar to that of 6, substituting propyl amine for methyl amine: (M+1)= 423.35

[(5-{6-[((3R)oxolan-3-yl)amino]purin-9-yl}(3S,2R,4R,5R)-3,4-dihydroxyoxolan-yl)methoxy]-N-butylcarboxamide (27)

This compound was prepared in a manner similar to that of 6, substituting n-butyl amine for methyl amine: (M+1)=437.39

[(5-{6-[((3R)oxolan-3-yl)amino]purin-9-yl}(3S,2R,4R,5R)-3,4-dihydroxy yl)methoxy]-N-cyclopentylcarboxamide (28)

This compound was prepared in a manner similar to that of 6, substituting cyclopentyl amine for methyl amine: (M+1)=449.38

[(5-{6-[((3R)oxolan-3-yl)amino]purin-9-yl}(3S,2R,4R,5R)-3,4-dihydroxyoxolan-2-yl)methoxy]-N-benzylcarboxamide (29)

This compound was prepared in a manner similar to that of 6, substituting benzyl amine for methyl amine: (M+1)=471.37

[(5-{6-[((3R)oxolan-3-yl)amino]purin-9-yl}(3S,2R,4R,5R)-3,4-dihydroxyoxolan-2-yl)methoxy]-N-[(4-fluorophenyl)methyl]carboxamide (30)

This compound was prepared in a manner similar to that of 6, substituting 4-fluorobenzyl amine for methyl amine: (M+1)=489.3

{(5-{6-[((3R)oxolan-3-yl)amino]purin-9-yl}(3S,2R,4R,5R)-3,4-dihydroxyoxolan-2-yl)methoxy]-N-cyclohexylcarboxamide (31)

This compound was prepared in a manner similar to that of 6, substituting cyclohexyl amine for methyl amine.

{(5-{6-[((3R)oxolan-3-yl)amino]purin-9-yl}(3S,2R,4R,5R)-3,4-dihydroxyoxolan-2-yl)methoxy]-N-(methylethyl)carboxamide (32)

This compound was prepared in a manner similar to that of 6, substituting i-propylamine for methyl amine: (M+1)=423.3

{(5-{6-[((3R)oxolan-3-yl)amino]purin-9-yl}(3S,2R,4R,5R)-3,4-dihydroxyoxolan-2-yl)methoxy]-N-cyclopropylcarboxamide (33)

This compound was prepared in a manner similar to that of 6, substituting cyclopropyl amine for methyl amine.

Methyl2-{[5-{6-[(3R)oxolan-3-yl)amino]purin-9-yl}(3S,2R,4R,5R)-3,4-dihydroxyoxolan-2-yl)methoxy]carbonylamino}cyclopentanecarboxylate (34)

This compound was prepared in a manner similar to that of 6, substituting 2-carbomethoxy cyclopentyl amine for methyl amine: (m+1)=507.31

Ethyl3-{[5-{6-[(3R)oxolan-3-yl)amino]purin-9-yl}(3S,2R,4R,5R)-3,4-dihydroxyoxolan-2-yl)methoxy]carbonylamino}(2S,3R)bicylo[2.2.1]hept-5-ene-2-carboxylate (35)

This compound was prepared in a manner similar to that of 6, substituting 2-carboethoxy norborn-5-enyl-2-amine for methyl amine: (M+1)=545.32

Ethyl3-{[5-{6-[(3R)oxolan-3-yl)amino]purin-9-yl}(3S,2R,4R,5R)-3,4-dihydroxyoxolan-2-yl)methoxy]carbonylamino}(2S,3R)bicylo[2.2.1]heptane-2-carboxylate (36)

This compound was prepared in a manner similar to that of 6, substituting 3-carboethoxy norborn-5-yl-2-amine for methyl amine: (M+1)=547.38

{(5-{6 [((3R)oxolan-3-yl)amino]purin-9-yl}(3S,2R,4R,5R)-3,4-dihydroxyoxolan-2-yl)methoxy]-N-[(1R,2R)-2-(phenylmethoxy)cyclopentyl]carboxamide (37)

This compound was prepared in a manner similar to that of 6, substituting (1R,2R)-2-benzyloxycyclopentyl amine for methyl amine: (M+1)=555.50

{(5-{6[((3R)oxolan-3-yl)amino]purin-9-yl}(3S,2R,4R,5R)-3,4-dihydroxyoxolan-2-yl)methoxy]-N-[(1S,2S)-2-(phenylmethoxy)cyclopentyl]carboxamide (38)

This compound was prepared in a manner similar to that of 6, substituting (1S,2S)-2-benzyloxycyclopentyl amine for methyl amine: (M+1)=555.50

[(5-{6-[((3R)oxolan-3-yl)amino}purin-9-yl}(3S,2R,4R,5R)-3,4-dihydroxyoxolan-2-yl)methoxy]-N-cyclobutylcarboxamide (39)

This compound was prepared in a manner similar to that of 6, substituting cyclobutyl amine for methyl amine: (M+1)=435.46.

(5-{6-[((3R)oxolan-3-yl)amino}purin-9-yl}(3S,2R,4R,5R)-3,4-dihydroxyoxolan-2-yl)methoxy]-N-(2-phenylcyclopropyl)carboxamide (40)

This compound was prepared in a manner similar to that of 6, substituting 2-phenylcyclopropyl amine for methyl amine: (M+1)=497.50

[(5-{6-[((3R)oxolan-3-yl)amino]purin-9-yl}(3S,2R,4R,5R)-3,4-dihydroxyoxolan-2-yl)methoxy]-N-prop-2-enylcarboxamide (41)

This compound was prepared in a manner similar to that of 6, substituting allyl amine for methyl amine: (M+1)=421.39

Ethyl 3-{[(5-{6-[((3R)oxolan-3-yl)amino]purin-9-yl}(3S, 2R,4R,5R)-3,4-dihydroxyoxolane-2-yl)methoxy}carbonylamino}propanoate (42)

This compound was prepared in a manner similar to that of 6, substituting ethyl 3-aminopropionate for methyl amine: (M+1)=481.37

Methyl 2-{[(5-{6-[((3R)oxolan-3-yl)amino]purin-9-yl}(3S, 2R,4R,5R) dihydroxyoxolane-2-yl)methoxy}carbonylamino}acetate (43)

This compound was prepared in a manner similar to that of 6, substituting methyl 2-aminoacetate for methyl amine: (M+1)=453.39

{(5-{6-[((3R)oxolan-3-yl)amino]purin-9-yl}(3S,2R,4R,5R)-3,4-dihydroxyoxolan-2-yl)methoxy]-N,N-dimethylcarboxamide (44)

Compound 44 was prepared in a manner similar to compound 6 substituting N,N-dimethyl amine for methyl amine.

2-{6-[((3R)oxolan-3-yl)amino]purin-9-yl}(4S,2R,3R,5R)-5-{[(methylamino)thioxomethoxy]methyl}oxolane-3,4-diol (45)

This compound was prepared in a manner similar to that of 6, substituting thiocarbonyl diimidazole(thioCDI) for carbonyl diimidazole(CDI): (M+1)=411.30

2-{6-[((3R)oxolan-3-yl)amino]purin-9-yl}(4S,2R, 3R,5R)-5-{[(ethylamino)thioxomethoxy] methyl}oxolane-3,4-diol (46)

This compound was prepared in a manner similar to that of 6, substituting thiocarbonyl diimidazole(thioCDI) for carbonyl diimidazole(CDI) and ethyl amine for methyl amine: (M+1)=425.30

2-{6-[((3R)oxolan-3-yl)amino]purin-9-yl}(4S,2R, 3R,5R)-5-({[(methylethyl)amino] thioxomethoxy}methyl)oxolane-3,4-diol (47)

This compound was prepared in a manner similar to that of 6, substituting thiocarbonyl diimidazole(thioCDI) for carbonyl diimidazole(CDI) and i-propyl amine for methyl amine: (M+1)=439.30

2-{6-[((3R)oxolan-3-yl)amino]purin-9-yl}(4S,2R, 3R,5R)-5-{[(butylamino)thioxomethoxy] methyl}oxolane-3,4-diol (48)

This compound was prepared in a manner similar to that of 6, substituting thiocarbonyl diimidazole(thioCDI) for carbonyl diimidazole(CDI) and n-butyl amine for methyl amine: (M+1)=453.30

2-{6-[((3R)oxolan-3-yl)amino]purin-9-yl}(4S,2R, 3R,5R)-5-{[(propylamino)thioxomethoxy] methyl}oxolane-3,4-diol (49)

This compound was prepared in a manner similar to that of 6, substituting thiocarbonyl diimidazole(thioCDI) for carbonyl diimidazole(CDI) and n-propyl amine for methyl amine: (M+1)=439.30

2-{6-[((3R)oxolan-3-yl)amino]purin-9-yl}(4S,2R, 3R,5R)-5-[(piperidylthioxomethoxy)methyl] oxolane-3,4-diol (50)

This compound was prepared in a manner similar to that of 6, substituting thiocarbonyl diimidazole(thioCDI) for carbonyl diimidazole(CDI) and piperidine for methyl amine: (M+1)=465.30

2-{6-[((3R)oxolan-3-yl)amino]purin-9-yl}(4S,2R, 3R,5R)-5-{[(cyclopentylamino)thioxomethoxy] methyl}oxolane-3,4-diol (51)

This compound was prepared in a manner similar to that of 6, substituting thiocarbonyl diimidazole(thioCDI) for carbonyl diimidazole(CDI) and cyclopentyl amine for methyl amine: (M+1)=465.30

2-{6-[((3R)oxolan-3-yl)amino]purin-9-yl}(4S,2R, 3R,5R)-5-[(pyrrolidinylthioxomethoxy)methyl] oxolane-3,4-diol (52)

This compound was prepared in a manner similar to that of 6, substituting thiocarbonyl diimidazole(thioCDI) for carbonyl diimidazole(CDI) and pyrrolidine for methyl amine: (M+1)=451.30

2-{6-[((3R)oxolan-3-yl)amino]purin-9-yl}(4S,2R, 3R,5R)-5-{[(dimethylamino)thioxomethoxy] methyl}oxolane-3,4-diol (53)

This compound was prepared in a manner similar to that of 6, substituting thiocarbonyl diimidazole(thioCDI) for carbonyl diimidazole(CDI) and N,N-dimethyl amine for methyl amine: (M+1)=425.30

2-{6-[((3R)oxolan-3-yl)amino]purin-9-yl}(4S,2R, 3R,5R)-5-({[benzylamino]thioxomethoxy}methyl) oxolane-3,4-diol (54)

This compound was prepared in a manner similar to that of 6, substituting thiocarbonyl diimidazole(thioCDI) for carbonyl diimidazole(CDI) and benzyl amine for methyl amine: (M+1)=487.30

2-{6-[((3R)oxolan-3-yl)amino]purin-9-yl}(4S,2R, 3R,5R)-5-({[cyclohexylamino] thioxomethoxy}methyl)oxolane-3,4-diol (55)

This compound was prepared in a manner similar to that of 6, substituting thiocarbonyl diimidazole(thioCDI) for carbonyl diimidazole(CDI) and cyclohexyl amine for methyl amine: (M+1)=479.30

2-{6-[((3R)oxolan-3-yl)amino]purin-9-yl}(4S,2R, 3R,5R)-5-[({[(1S,2S)-2-(phenylmethoxy) cyclopentyl]amino}thioxomethoxy)methyl]oxolane-3,4-diol (56)

This compound was prepared in a manner similar to that of 6, substituting thiocarbonyl diimidazole(thioCDI) for carbonyl diimidazole(CDI) and (i S,2S)-2-benzyloxycyclopentyl amine for methyl amine: (M+1)= 571.47

2-{6-[((3R)oxolan-3-yl)amino]purin-9-yl}(4S,2R, 3R,5R)-5-[(([(1R,2R)-2-(phenylmethoxy) cyclopentyl]amino}thioxomethoxy)methyl]oxolane-3,4-diol (57)

This compound was prepared in a manner similar to that of 6, substituting thiocarbonyl diimidazole(thioCDI) for carbonyl diimidazole(CDI) and (1R,2R)-2-benzyloxycyclopentyl amine for methyl amine: (M+1)= 571.47

2-{6-[((3)oxolan-3-yl)amino]purin-9-yl}(4S,2R,3R, 5R)-5{[(cyclobutylamino)thioxomethoxy] methyl}oxolane-3,4-diol (58)2

This compound was prepared in a manner similar to that of 6, substituting thiocarbonyl diimidazole(thioCDI) for carbonyl diimidazole(CDI) and cyclobutyl amine for methyl amine: (M+1)=451.44

2-{6-[((3R)oxolan-3-yl)amino]purin-9-yl}(4S,2R, 3R,5R)-5-{[(cyclopropylamino)thioxomethoxy] methyl}oxolane-3,4-diol (59)

This compound was prepared in a manner similar to that of 6, substituting thiocarbonyl diimidazole(thioCDI) for carbonyl diimidazole(CDI) and cyclopropyl amine for methyl amine: (M+1)=437.43.

2-{6-[((3R)oxolan-3-yl)amino]purin-9-yl}(4S,2R, 3R,5R)-5-{[(prop-2-enylamino)thioxomethoxy] methyl}oxolane-3,4-diol (60)

This compound was prepared in a manner similar to that of 6, substituting thiocarbonyl diimidazole(thioCDI) for carbonyl diimidazole(CDI) and allyl amine for methyl amine: (M+1)=437.43.

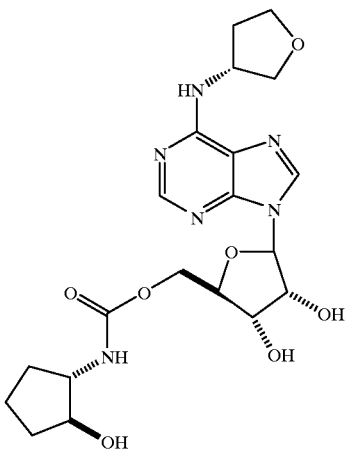

{(5-{6 ((3R)oxolan-3-yl)amino]purin-9-yl)(3S,2R, 4R,5R)-3,4-dihydroxyoxolan-2-yl)methoxy]-N-((1S, 2S)-2-hydroxycyclopentyl)carboxamide (61)

Compound 38 (25 mg), ethanol (5 mL), cyclohexene (5 mL), and palladium hydroxide on carbon (50 mg) were mixed and refluxed for 48 h. The catalyst was filtered through celite by gravity filtration and the solvent was removed under reduced pressure to give 61.

{(5-{6[((3R)oxolan-3-yl)amino]purin-9-yl}(3S,2R, 4R,5R)-3,4-dihydroxyoxolan-2-yl)methoxy]-N-((1R, 2R)-2-hydroxycyclopentyl)carboxamide (62)

This compound was prepared from 37 using the procedure similar to that used for 61: (M+1)=465.29

2-{6-[((3R)oxolan-3-yl)amino]purin-9-yl}(4S,2R, 3R,5R)-5-({[((1R,2R)-2-hydroxycyclopentyl)amino] thioxomethoxy}methyl)oxolane-3,4-diol (63)

This compound was prepared from 57 using the procedure similar to that used for 61: (M+1)=465.29.

2-{6-[((3R)oxolan-3-yl)amino]purin-9-yl}(4S,2R, 3R,5R)-5-({[((1S,2S)-2-hydroxycyclopentyl)amino] thioxomethoxy}methyl)oxolane-3,4-diol (64)

This compound was prepared from 56 using the procedure similar to that used for 61: (M+1)=465.29.

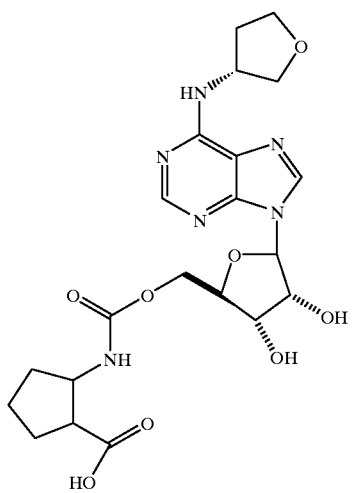

2-{[5-6-[(3R)oxolan-3-yl)amino]purin-9-yl}(3S,2R, 4R,5R)-3,4-dihydroxyoxolan-2-yl)methoxy] carbonylamino}cyclopentanecarboxylic acid (65)

To a cooled (0° C.) solution of ester 34 (12 mg) in 2:1 THF:H2O (2 mL) was added 3 eq. of lithium hydroxide monohydrate (2M solution in water). The reaction was allowed to stir at 0° C. for 2 hours, then allowed to warm to room temperature for 30 minutes. After all the ester was consumed as judged by TLC, amberlite resin (approximately 4 mg) was added and the solution was filtered through a cotton plug. Evaporation of solvent gave the pure acid 65.

3-{[(5-{6-[((3R)oxolan-3-yl)amino]purin-9-yl}(3S, 2R,4R,5R)-3,4dihydroxyoxolan-2-yl)methoxy] carbonylamino}(2S,3R)bicyclo[2.2.1]hept-5-ene-2-carboxylic acid (66)

This compound was prepared from compound 35 using the procedure similar to that used for 65: (m+1)=517.35

3-{[(5-{6-[((3R)oxolan-3-yl)amino]purin-9-yl}(3S, 2R,4R,5R)-3,4 dihydroxyoxolan-2-yl)methoxy] carbonylamino}propanoic acid (67)

This compound was prepared from compound 42 using the procedure similar to that used for 65:(m+1)=453.32

2-{[(5-{6-[((3R)oxolan-3-yl)amino]purin-9-yl}(3S, 2R,4R,5R)-3,4 dihydroxyoxolan-2-yl)methoxy] carbonylamino}acetic acid (68)

This compound was prepared from compound 43 using the procedure similar to that used for 65: (m+1)=439.30

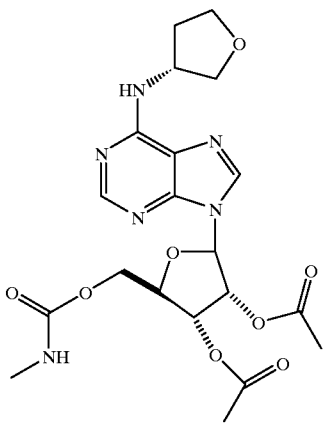

5-{6-[((3R)oxolan-3-yl)amino]purin-9-yl}(2R,3R,
4R,5R)-4-acetyloxy-2-[(N-methylcarbamoyloxy)
methyl]oxolan-3-yl acetate (7)

To a solution of compound 6 (70 mg) and dimethylaminopyridine (50 mg) in pyridine (2 mL) at 23° C. was added acetic anhydride (0.1 mL). After 3 h at 23° C., the reaction was concentrated in vacuo. The residue was dissolved in methylene chloride (50 mL), washed with water (3×10 mL), and dried (Na$_2$SO$_4$). After concentration in vacuo, the residue was purified by flash chromatography (methylene chloride:methanol 20:1 followed by 9:1) to afford compound 7 (70 mg).

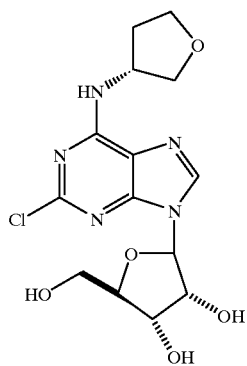

2-{6-[((3R)oxolan-3-yl)amino]-2-chloropurin-9-yl}
(4S,2R,3R,5R)-5-(hydroxymethyl)oxolane-3,4-diol
(10)

Compound 8 was prepared from 1,2,3,4-tetra-O-acetylribofuranoside 2 and 2,6-dichloropurine following the procedure reported in the literature (John A. Montgomery et. al. J. Heterocycl. Chem. 1964, 213.) A mixture of compound 8 (1. g, 2.24 mmol) and (R)-3-amino tetrahydrofuran (tosylate salt) (0.75 g, 3 mmol) in methanol were stirred for 16 h. Methanol was evaporated under reduced pressure and the residue was filtered through a plug of silica gel to give a gum. An NMR spectrum of this gum showed peaks corresponding to compound 9. This material was used without further purification in the next reaction.

To the material from the previous reaction, methanolic ammonia (0.5 M, 20 mL) was added and stirred for 16 h at room temperature. The solvent was removed under reduced pressure and the residue was purified by silica gel column chromatography (10% methanol-ethyl acetate) to give compound 10 as a white solid.

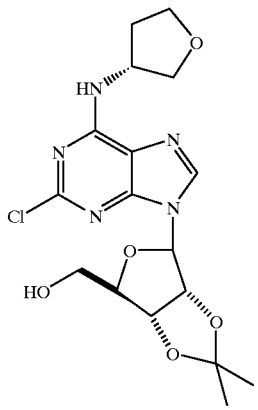

(4-{6-[((3R)oxolan-3-yl)amino]-2-chloropurin-9-yl}
(1R,2R,4R,5R)-7,7-dimethyl-3,6,8-trioxabicyclo
[3.3.0]oct-2-yl)methan-1-ol (11)

To a solution of compound 1 (0.36, 1 mmol)) and 2,2-dimethoxypropane (0.2 g, 2 mmol) in dimethylformamide (5 mL) was added p-toluenesulfonic acid (10 mg) at 70° C. After 48 h at 70° C., the reaction was concentrated in vacuo to afford a solid. The solid was dissolved in methanol (1 mL), then triturated with ethyl ether (50 mL). The resultant crystals were collected by vacuum filtration to afford the intermediate 11.

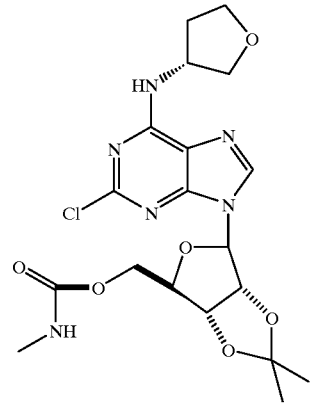

[(4-{6-[((3R)oxolan-3-1)amino]-2-chloropurin-9-yl}
(1R,2R,4R,5R)-7,7-dimethyl-3,6,8-trioxabicyclo
[3.3.0]oct-2-yl)methoxy]-N-methylcarboxamide (12)

To a solution of compound 11 (90 mg, 0.25 mmol) in THF (1 mL) was added carbonyldiimidazole (162 mg, 1 mmol) at rt. After stirring for 2 h, excess reagent was quenched by adding a drop of water. Methylamine (40% aq. Solution, 0.5 mL) was added and stirring was continued for another 16 h. The reaction mixture was concentrated in vacuo to afford a gum. It was purified by prep.TLC [(silica gel, 10% MeOH-dichloromethane)] to afford compound 12.

[(5-{6-[((3R)oxolan-3-yl)amino]-2-chloropurin-9-yl}(3S,2R,4R,5R)-3,4-dihydroxyoxolan-2-yl)methoxy]-N-methylcarboxamide (13)

Compound 12 (50 mg) was taken in a mixture of acetic acid (8 mL) and water (2 mL) and heated at 90° C. for 16 h. Solvents were removed under reduced pressure and the residue was purified by preparative TLC [methanol-dichloromethane (1:9)] to afford compound 13.

[(5-{6-[((3R)oxolan-3-yl)amino]-2-chloropurin-9-yl}(3S,2R,4R,5R)-3,4-dihydroxyoxolan-2-yl)methoxy]-N-cyclopentylcarboxamide (69)

This compound was prepared in a manner similar to that of 13 substituting cyclopentyl amine for methyl amine.

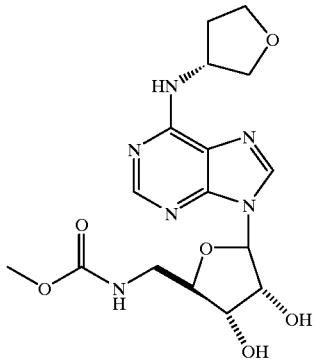

N-[(5-{6-[I((3R)oxolan-3-yl)amino]purin-9-yl}(3S,2R,4R,5R)-3,4-dihydroxyoxolan-2-yl) methyl] methoxycarboxamide (18)

Compound 14 (1.4 g, 3.07 mmol) was dissolved in dry DMF and sodium azide (3.00 g, 4.6 mmol) was added and heated at 65° C. for 16 h. The solvent was evaporated and the residue was subjected to aqueous work up and purified by flash column (100% ethyl acetate) to get 15.

A solution of 15 (314 mg) in ethanol containing 10% Pd—C (100 mg) in an atmosphere of hydrogen was stirred at room temperature for 16 h. Filtration followed by the evaporation of solvent gave compound 16.

CDI (100 mg) was added to 3 mL of dry methanol and stirred at room temeprature for 15 min. The solvent was evaporated and the residue was dissolved in dry THF (5 mL). Compound 16 (25 mg) was added to the solution and the mixture was stirred at room temperature for 16 h. The solvent on evaporation followed by preparative TLC (5% MeOH: 95% DCM) purification gave the compound 17. Deprotection of 17 with 80% aqueous acetic acid followed by evaporation and purification by preparative TLC (5% MeOH: 95% DCM) gave compound 18 [MS 395.2 (M+1)].

N-[(5-{6-[((3R)oxolan-3-yl)amino]purin-9-yl}(3S,2R,4R,5R)-3,4-dihydroxyoxolan-2-yl)methy] cyclopentyloxycarboxamide (70)

Compound 70 was prepared as described above substituting cyclopentanol for methanol [MS 489.3 (M+1)].

2-{6-[((3R)oxolan-3-yl)amino]purin-9-yl}(4S,2R,3R,5R)-5-{[methoxythioxomethyl)amino]methyl}oxolane-3,4-diol (71)

Compound 71 was prepared as described above substituting thioCDI for CDI [MS 411.2 (M+1)].

2-{6-[((3R)oxolan-3-yl)amino]purin-9-yl}(4S,2R,3R,5R)-5-{[cyclopentyloxythioxomethyl)amino]methyl}oxolane-3,4-diol (72)

Compound 72 was prepared as described above substituting thioCDI for CDI and cyclopentanol for methanol [MS 465.7 (M+1)].

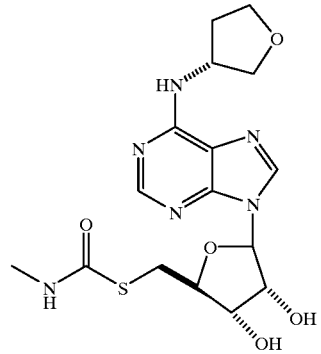

[(5-{6-[((3R)oxolan-3-yl)amino]purin-9-yl}(2S,3S,4R,5R)-3,4-dihydroxyoxolan-2-yl)methythio]-N-methylcarboxamide (22)

To a solution of compound 15 (455 mg) in acetone (30 mL) potassium thioacetate was added and refluxed for 16 h. The reaction mixture was cooled and the solvent was evaporated. Purification of the residue by flash column chromatography (100% ethyl acetate) gave compound 19.

Sodium methoxide in methanol (0.5M; 9 mL) was added to 19 (570 mg) and the resulting solution was stirred under nitrogen at room temperature for 4 h. An aliquot of the reaction mixture was worked up and the product was analyzed by NMR to see the disappearance of the acetate peak (2.3 ppm). The reaction mixture was subjected to aqueous work up and the product was extracted with DCM. Care was taken to purge the solvents, that are used for the work up, with nitrogen for at least 30 min to minimize the oxidation of thiol to the disulfide. The organic layer on evaporation gave compound 20.

Nitrogen was bubbled for 30 min through 10 mL of acetonitrile containing about 2 mg of DMAP. Compound 20 was added to the above solution followed by the addition of methyl isocyanate. The mixture was stirred at room temperature for 16 h under nitrogen. The completion of the reaction was checked by TLC (5% MeOH:95% DCM). Purification of the residue obtained by the evaporation of the reaction mizture gave compound 22 [MS 411.2 (M+1)].

[(5-{6-[((3R)oxolan-3-yl)amino]purin-9-yl}(2S,3S,4R,5R)-3,4-dihydroxyoxolan-2-yl)methythio]-N-cyclopentylcarboxamide (73)

Compound 73 was prepared in the manner of compound 22 by substituting cyclopentyl isocyanate for methyl isocyanate [MS 465.2 (M+1)].

2-{6-[((3R)oxolan-3-yl)amino]purin-9-yl}(4S,5S,2R,3R)-5-{[(methylamino)thioxomethylthio]methyl}oxolane-3,4-diol (74)

Compound 74 was prepared in the manner of compound 22 by substituting methyl isothiocyanate for methyl isocyanate [MS 427.2 (M+1)].

2-16-[((3R)oxolan-3-yl)amino]purin-9-yl}(4S,5S,2R,3R)-5-{[(cyclopentylamino)thioxomethylthio]methyl}oxolane-3,4-diol (75)

Compound 75 was prepared in the manner of compound 22 by substituting cyclopentyl isothiocyanate for methyl isocyanate [MS 481.2 (M+1)].

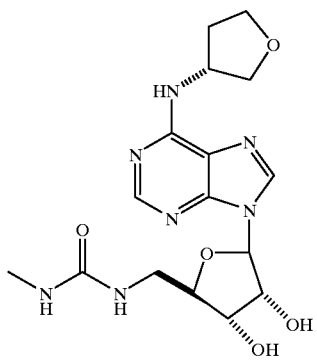

24

N-[(5-{6-[((3R)oxolan-3-yl)amino]purin-9-yl}(3S,2R,4R,5R)-3,4-dihydroxyoxolan-2-yl)methyl](methylamino)carboxamide (24)

To a solution of 16 (30 mg) in acetonitrile a small amount (2 mg) of DMAP followed by methyl isocyanate (250 μL) was added and stirred at room temperature for 16 h. The solvent was evaporated and the residue was purified by preparative TLC (5% MeOH:95% DCM) to obtain compound 23. Deprotection of 22 with 80% aqueous acetic acid followed by preparative TLC purification (5% MeOH:95% DCM) gave compound 24 [MS 394.2 (M+1)].

N-[(5-{6-[((3R)oxolan-3-yl)amino]purin-9-yl}(3S,2R,4R,5R)-3,4-dihydroxyoxolan-2-yl)methyl](cyclopentylamino)carboxamide (76)

Compound 76 was prepared in the manner of compound 24 substituting cyclopentyl isocyanate for methyl isocyanate and refluxing for 16 h [MS 448.3 (M+1)].

2-{6-[((3R)oxolan-3-yl)amino]purin-9-yl}(4S,2R,3R,5R)-5-({[(methylamino)thioxomethyl]amino}methyl)oxolane-3,4-diol (77)

Compound 77 was prepared in the manner of compound 24 substituting methyl isothiocyanate for methyl isocyanate and refluxing for 16 h [MS 410.3 (M+1)]. 2-{6-[((3R)oxolan-3-yl)amino]purin-9-yl}(4S,2R,3R,5R)-5-({[(cyclopentylamino)thioxomethyl]amino}methyl)oxolane-3,4-diol (78) Compound 78 was prepared in the manner of compound 24 substituting cyclopentyl isothiocyanate for methyl isocyanate and refluxing for 16 h [MS 464.3 (M+1)].

N-[(5-{6-[((3R)oxolan-3-yl)amino]purin-9-yl}(3S,2R,4R,5R)-3,4dihydroxyoxolan-2-yl)methyl](ethylamino)carboxamide (79)

Compound 79 was prepared in the manner of compound 24 substituting ethylisocyanate for methyl isocyanate and refluxing for 16 h [MS 408 (M+1)].

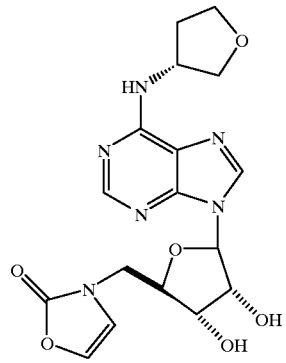

80

3-[(5-{6-[((3R)oxolan-3-yl)amino]purin-9-yl}(3S,2R,4R)-3,4-dihydroxyoxolan-2-yl)methyl]-1,3-oxazolin-2-one (80)

Sodium hydride (40 mg, 60% in mineral oil) was added to a solution of oxazolidinone (85 mg, 1 mmol) in anhydrous DMF (2 mL). To this was added a solution of compound 15 (100 mg) in DMF (2 mL). Reaction mixture was allowed to stir at RT for 3 h. The solvent was removed under reduced pressure, the residue was dissolved in 80% acetic acid/water and heated at 80° C. for 16 h. Solvent was removed under reduced pressure and the residue was purified by preparative TLC (10% methanol-dichloromethane) to give compound 80 as a solid: (M+1)=405.38.

2-{6-[((3R)oxolan-3-yl)amino]-2-chloropurin-9-yl}(4S,2R,3R,5R)-5-1[(methylamino)thioxomethoxy]methyl}oxolane-3,4-diol (81)

This compound was prepared in a manner similar to that of 13, substituting thiocarbonyl diimidazole(thioCDI) for carbonyl diimidazole(CDI). (M+1)=445.28

2-{6-[((3R)oxolan-3-yl)amino]-2-chloropurin-9-yl}(4S,2R,3R,5R)-5-{[(ethylamino)thioxomethoxy]methyl}oxolane-3,4-diol (82)

This compound was prepared in a manner similar to that of 13, substituting thiocarbonyl diimidazole(thioCDI) for carbonyl diimidazole(CDI) and ethylamine for methylamine. (M+1)=459.29

2-{6-[((3R)oxolan-3-yl)amino]-2-chloropurin-9-yl}(4S,2R,3R,5R)-5-{[(propylamino)thioxomethoxy]methyl}oxolane-3,4-diol (83)

This compound was prepared in a manner similar to that of 13, substituting thiocarbonyl diimidazole(thioCDI) for carbonyl diimidazole(CDI) and propylamine for methylamine

2-({[5-{6-[((3R)oxolan-3-yl)amino]purin-3-yl}(3S,2R,4R,5R)-3,4-dihydroxyoxolan-2-yl)methoxy]thioxomethyl}amino)cyclopentanecarboxylic acid (84)

This compound was prepared from compound 85 using the procedure similar to that used for 65: (M+1)=509.24

Methyl 2-({[5-{6-[((3R)oxolan-3-yl)amino]purin-3-yl}(3S,2R,4R,5R)-3,4-dihydroxyoxolan-2-yl)methoxy]thioxomethyl}amino)cyclopentanecarboxylate (85)

This compound was prepared in a manner similar to that of 6, substituting thiocarbonyl diimidazole(thioCDI) for carbonyl diimidazole(CDI) and 2-carboethoxycyclopentyl amine for methyl amine. (M+1)=523.29

Ethyl 3-({[5-{6-[((3R)oxolan-3-yl)amino]purin-3-yl}(3S,2R,4R,5R)-3,4-dihydroxyoxolan-2-yl)methoxy]thioxomethyl}amino)propanoate (86)

This compound was prepared in a manner similar to that of 6, substituting thiocarbonyl diimidazole(thioCDI) for carbonyl diimidazole(CDI) and ethyl 3-aminopropionate for methyl amine. (M+1)=497.28

Ethyl 3-({[5-{6-[((3R)oxolan-3-yl)amino]purin-3-yl}(3S,2R,4R,5R)-dihydroxyoxolan-2-yl)methoxy]thioxomethyl}amino)(2S,3R)bicyclo[2.2.1]hept-5-ene-2-carboxylate (87)

This compound was prepared in a manner similar to that of 6, substituting thiocarbonyl diimidazole(thioCDI) for carbonyl diimidazole(CDI) and 2-carboethoxynorborn-5-enyl-2-amine for methyl amine. (M+1)=561.31

5-{6-[((3R)oxolan-3-yl)amino]purin-9-yl}(2R,3R,4R,5R)-4-acetyloxy-2-{[(propylamino)thioxomethoxy]methyl}oxolan-3-yl acetate (88)

This compound was prepared from 49 using the procedure similar to that of 7. 5-{6-[((3R)oxolan-3-yl)amino]purin-9-yl}(2R,3R,4R,5R)-4-acetyloxy-2-[(N-cyclopentylcarbamoyloxy)methyl]oxolan-3-yl acetate(89)

This compound was prepared from 28 using the procedure similar to that of 7. (M+1)=533.5

5-{6-[((3R)oxolan-3-yl)amino]purin-9-yl}(2R,3R,4R,5R)-4-acetyloxy-2-{[(methylamino)thioxomethoxy]methyl}oxolan-3-yl acetate (90)

This compound was prepared from 45 using the procedure similar to that of 7. (M+1)=495.5

N-[(5-{6-[((3R)oxolan-3-yl)amino]purin-9-yl}(3S,2R,4R,5R)-3,4-dihydroxyoxolan-2-yl)methyl](dimethylamino)carboxamide (92)

To a solution of 16 in dichloromethane triethylamine and N,N-dimethylcarbamoyl chloride were added and stirred at room temperature for 16 h. The solvent was evaporated and the residue was purified by flash column chromatography (2% MeOH:98% DCM) isopropylidine protected compound 92. Deprotection with 80% aqueous acetic acid followed by preparative TLC purification (5% MeOH:95% DCM) gave compound 92 [MS 408.3 (M+1)].

N-[(5-{6-[((3R)oxolan-3-yl)amino]purin-9-yl}(3S,2R,4R,5R)-3,4-dihydroxyoxolan-2-yl)methyl](propylamino)carboxamide (93)

Compound 93 was prepared in the manner of compound 24 substituting propyl isocyanate for methyl isocyanate and refluxing for 16 h [MS 422.3 (M+1)].

2-16-[((3R)oxolan-3-yl)amino]purin-9-yl}(4S,2R,3R,5R)-5-({[propylamino)thioxomethyl]amino}methyl)oxolane3,4-diol (94)

Compound 94 was prepared in the manner of compound 24 substituting propyl isocyanate for methyl isocyanate and refluxing for 16 h [MS 438.3 (M+1)].

Scheme

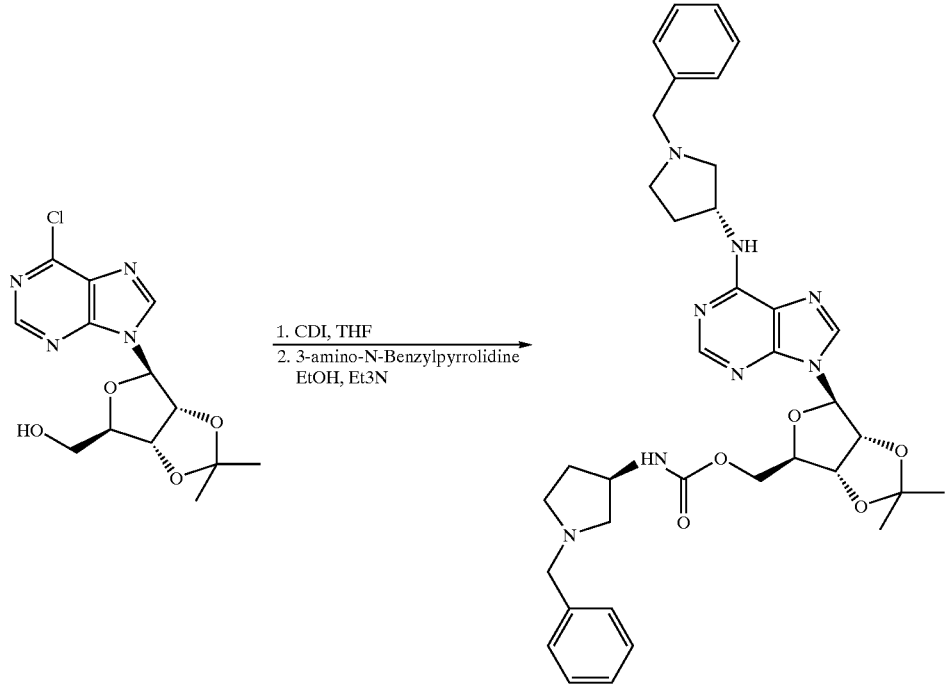

-continued

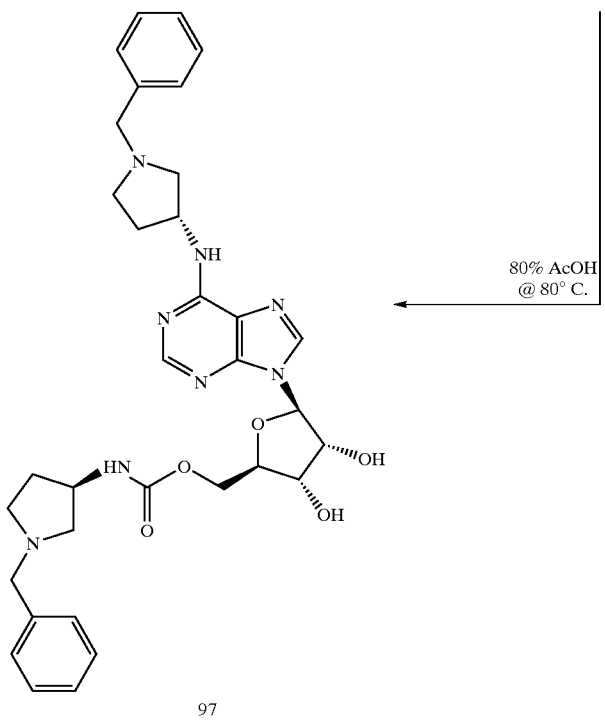

97

The above scheme follows the same procedure as previously described schemes, but uses a nitrogen heterocyclyl instead of oxygen heterocyclyl.

To a solution of compound 95 (1.0 g, 3.06 mmol) in Tetrahydrofuran (25 mL) was added 1,1'-Carbonyldiimidazole (0.55 g, 3.37 mmol) and let stir. After 18 h of stirring at ambient temperature, excess 1,1'—Carboyldiimidazole was quenched with water (3 mL), added 3-amino-N-benzylpyrrolidine (1.61 g, 9.2 mmoles) and refluxed for 24 hours. The solvent was evaporated under vacuum and the crude product was purified by flash column chromatography (100% EtOAc-5% Methanol/Dichloromethane) to give a brown solid (96). (M+1)=669.8

Compound 96 (700 mg) was dissolved in a mixture of acetic acid (40 mL) and water (10 mL) and heated at 80° C. for 16 h. Solvents were removed under reduced pressure. The residue was diluted with dichloromethane (250 mL), washed the organic phase with 10% NaOH solution (2×50 mL), combined the organic phases and dried over MgSO$_4$, evaporated to dryness. The crude product was then purified by flash column chromatography [methanol-dichloromethane (15:85)] to afford compound 97 as pale yellow solid. (M+1) 629.71

N-[(3R)-1-benzylpyrrolidin-3-yl]{[5-(6-{[(3R)-1-benzylpyrrolidin-3-yl]amino}purin-9-yl)(3S,2R,4R,5R)-3,4-dihydroxyoxolan-2-yl]methoxy}carboxamide (97)

$A_1$-agonist stimulated [$^{35}$S]GTPγS binding of several compounds of this example was determined by the method set forth in Example 1, above. The assay results are set forth in Table 1, below.

TABLE 1

| Compound # | GTPγS |
|---|---|
| CPA | 100% |
| 41 | 48% |
| 39 | 67% |
| 63 | 100% |
| 64 | 99% |
| 71 | 98% |
| 74 | 95% |
| 72 | 93% |
| 59 | 82% |
| 65 | 81% |
| 80 | 80% |
| 72 | 93% |
| 18 | 77% |
| 70 | 76% |
| 58 | 79% |
| 57 | 67% |
| 39 | 67% |
| 61 | 59% |
| 43 | 53% |
| 35 | 52% |
| 56 | 52% |
| 69 | 50% |
| 42 | 47% |
| 62 | 42% |
| 36 | 41% |
| 37 | 30% |
| 34 | 17% |
| 38 | 1% |
| 40 | −6% |
| 6 | 48% |
| 77 | 101% |
| 78 | 95% |
| 13 | 77% |
| 73 | 109% |
| 75 | 91% |
| 22 | 98% |
| 67 | 59% |
| 68 | 76% |
| 22 | 98% |
| 75 | 91% |

| | |
|---|---|
| 69 | 50% |
| 45 | 77% |
| 45 | 77% |
| 46 | 77% |
| 49 | 89% |
| 47 | 84% |
| 48 | 70% |
| 25 | 80% |
| 27 | 44% |
| 26 | 73% |
| 32 | 91% |
| 54 | 93% |
| 60 | 77% |
| 53 | 85% |
| 55 | 82% |
| 52 | 77% |
| 50 | 88% |
| 30 | 41% |
| 28 | 69% |

Example 3

The compounds of this example are prepared as outlined in Schemes 1–4, below. Compounds having the general formula IV can be prepared as shown in Scheme 1. Compound I can be prepared through reaction of the corresponding primary amino compound, $R^1NH_2$, through heating with commercially available 6-chloroadenosine in the appropriate solvent (eg. n-butanol, dimethylformamide, and ethanol). The primary amino compound, $R^1NH_2$, is either commercially available or can be prepared as previously described in U.S. Pat. No. 5,789,416, the specification of which is incorporated herein by reference. The pro-drug esters of this invention can be prepared using all of the known methods for ester formation which are included by reference (see Jerry March Organic synthesis and Richard Larock—Methods of Organic Synthesis), and more preferably by those outlined in this application.

The key intermediate compound III can be prepared by the direct chlorination of the 2',3',5'-tri-O-acetyl-$N^6$-substitued adenosine (II). Compound II can be obtained by substitution of 6-chloropurine riboside with an amine (Fleysher, M. H. J. Med. Chem. 1972, 15, 187–191) followed by acetylation of the formed $N^6$-substituted adenosine (compound I). Nucleophilic displacement of the chlorine atom of compound III with different alkyl amines results in the formation of C-8 substituted compounds with simultaneous deacetylation to yield compound IV (Harlof Roelen et al. J. Med. Chem. 1996, 39, 1463–1471).

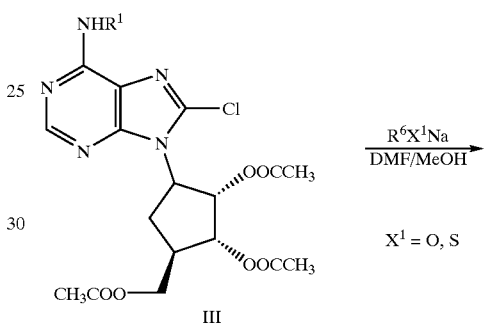

SCHEME 2

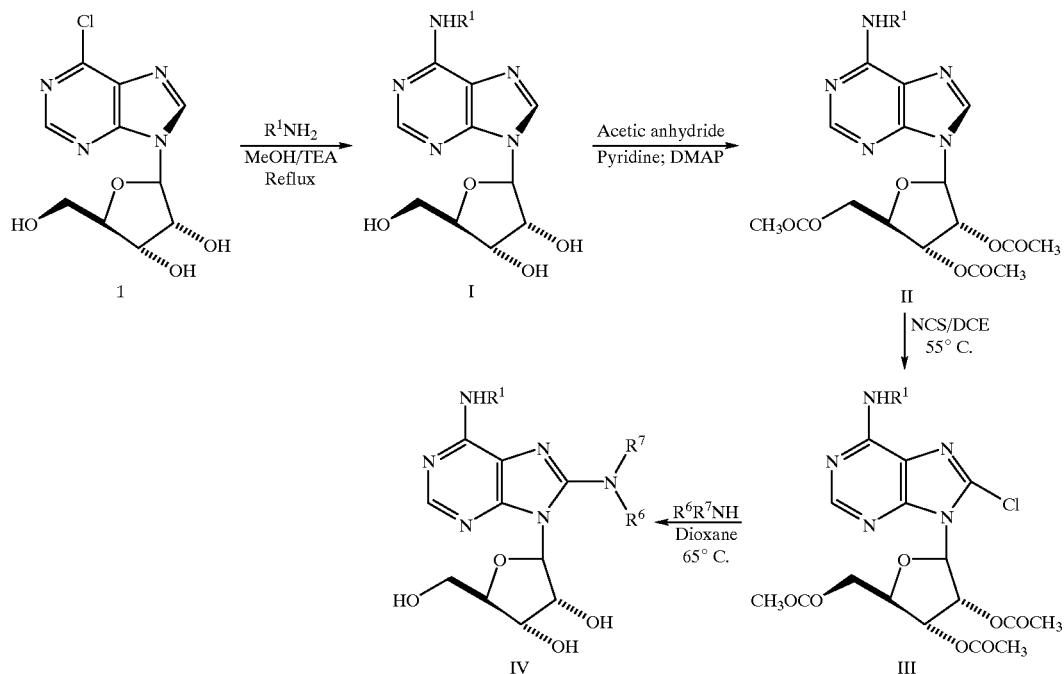

SCHEME 1

-continued
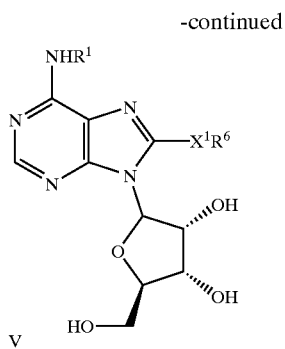
V
Compounds with the general structure V can be prepared by the reaction of compound III or compound I (scheme 1) with sodium aryloxide, alkoxide, arylthiolate or alkylthiolate in alcohol or DMF at room temperature or reflux conditions (G. Buenger and V. Nair, Synthesis, 1990, p 962–966).
SCHEME 3
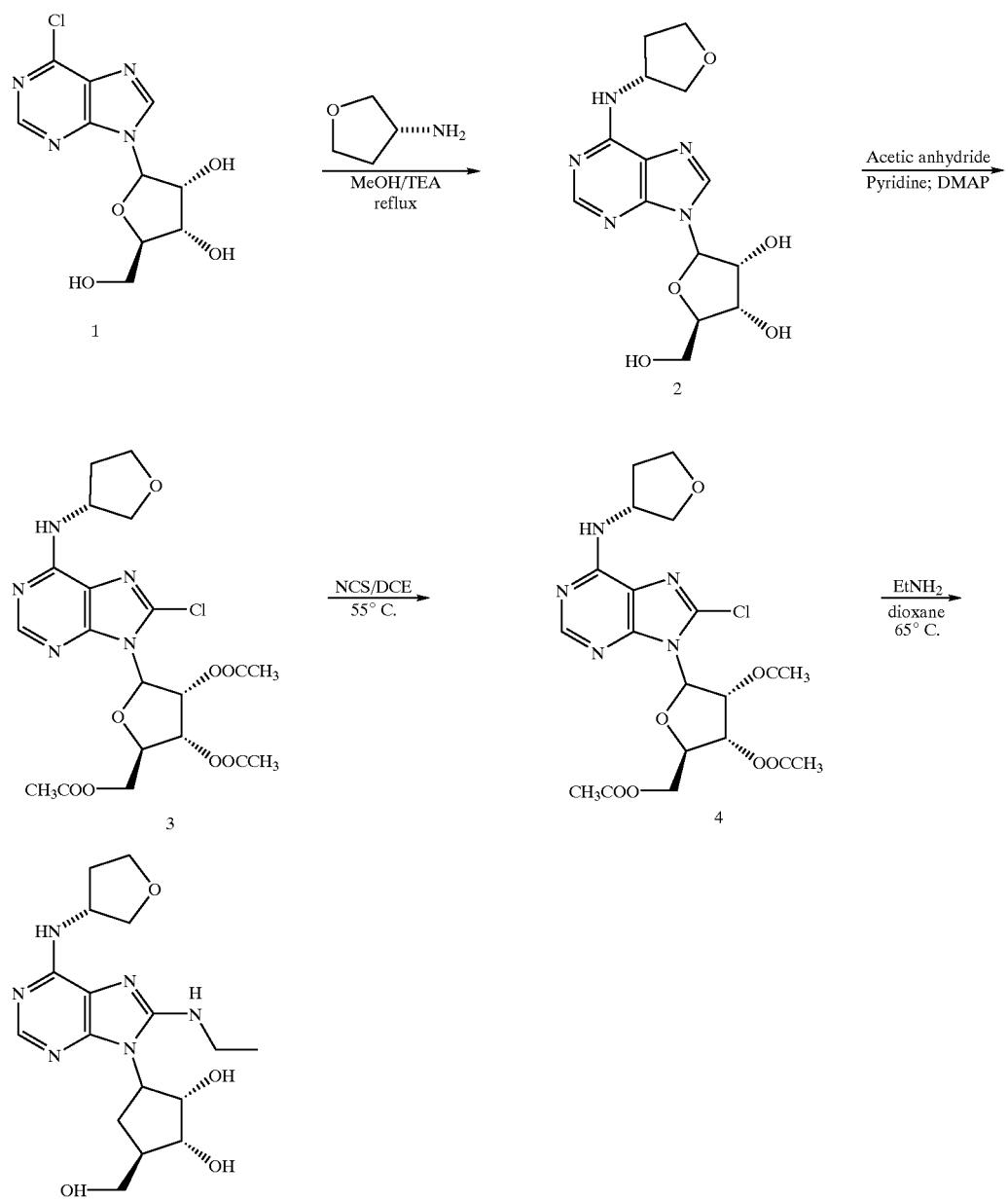

The preparation of compound 2 has been described previously in U.S. Pat. No. 5,789,416. Compound 4 has been obtained by the direct chlorination of compound 3 that has been prepared by the acetylation of compound 2. Nucleophilic displacement of the chlorine atom with ethylamine resulted in the formation of compound 5.

SCHEME 4

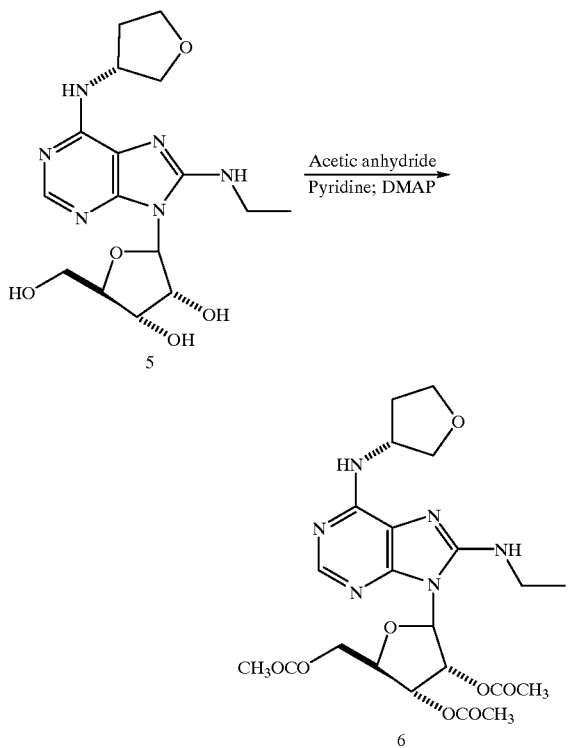

Compound 6 can be obtained by the direct acetylation of compound 5 (Scheme 4).

2-{6-[((3R)oxolan-3-yl)amino]-8-(ethylamino)purin-9-yl}(4S,2R,3R,5R)-5-(hydroxymethyl)oxolane-3,4-diol (Compound 5)

(5-{6-[((3R)oxolan-3-yl)amino]-8-(ethylamino)purin-9-yl}(2R,3R,4R,5R)-3,4-diacetyloxyoxolan-2-yl)methyl acetate (compound 6)

Compound 6 was prepared as described for the synthesis of compound B above.

2-{6-[((3R)oxolan-3-yl)amino]-8-(methylamino)purin-9-yl}(4S,2R,3R,5R)-5-(hydroxymethyl)oxolane-3,4-diol (compound 7)

Compound 7 was prepared as described above substituting methylamine for ethylamine.

2-{6-[((3R)oxolan-3-yl)amino]-8-(propylamino)purin-9-yl}(4S,2R,3R,5R)-5-(hydroxymethyl)oxolane-3,4-diol (compound 8)

Compound 8 was prepared as described above substituting n-propylamine for ethylamine.

2-{6-[((3R)oxolan-3-yl)amino]-8-(butylamino)purin-9-yl}(4S,2R,3R,5R) (hydroxymethyl)oxolane-3,4-diol (compound 9)

Compound 9 was prepared as described above substituting n-butylamine for ethylamine.

2-{6-[((3R)oxolan-3-yl)amino]-8-[benzylamino]purin-9-yl}(4S,2R,3R,5R)-5-(hydroxymethyl)oxolane-3,4-diol (compound 10)

Compound 10 was prepared as described in example 1. Substituting benzylamine for ethylamine.

2-{6-[((3R)oxolan-3-yl)amino]-8-[(methylethyl)amino]purin-9-yl}(4S,2R,3R,5R)-5-(hydroxymethyl)oxolane-3,4-diol (compound 11)

Compound 11 was prepared as described in example 1 substituting isopropylamine for ethylamine.

2-{6-[((3R)oxolan-3-yl)amino]-8-(prop-2-enylamino)purin-9-yl}(4S,2R,3R,5R)-5-(hydroxymethyl)oxolane-3,4-diol (compound 12)

Compound 12 was prepared as described in example 1 substituting allylamine for ethylamine [(MS: 393.7 (M+1)].

2-{6-[((3R)oxolan-3-yl)amino]-8-(prop-2-ynylamino)purin-9-yl}(4S,2R,3R,5R)-5-(hydroxymethyl)oxolane-3,4-diol (compound 13)

Compound 13 was prepared as described in example 1 substituting propargylamine for ethylamine[MS: 391.37 (M+1)].

2-{6-[((3R)oxolan-3-yl)amino]-8-methoxypurin-9-yl}(4S,2R,3R,5R)-5-(hydroxymethyl)oxolane-3,4-diol (compound 13)

To a solution of compound C in 1 mL of dry methanol was added 3 mL of 0.5M solution of sodium methoxide in methanol. The reaction mixture was refluxed for 30 min. TLC (5% MeOH:95% DCM) showed that the reaction was completed. The reaction mixture was cooled and quenched with a few drops of glacial acetic acid and the solvent was evaporated. The residue was taken up in methanol and analyzed by mass spectrometer [MS 368.2 (M+1) and 390.2 (M+23)].

2-{6-[((3R)oxolan-3-yl)amino]-8-(prop-2-ynylamino)purin-9-yl}(4S,2R,3R,5(hydroxymethyl)oxolane-3,4-diol (compound 13)

Compound 13 was prepared as described above substituting propargylamine for ethylamine [MS: 391.37 (M+1)].

2-{6-[((3R)oxolan-3-yl)amino]-8-methoxypurin-9-yl}(4S,2R,3R,5R)-5-(hydroxymethyl)oxolane-3,4-diol (compound 14)

To a solution of compound 4 in 1 mL of dry methanol was added 3 mL of 0.5M solution of sodium methoxide in methanol. The reaction mixture was refluxed for 30 min. TLC (5% MeOH:95% DCM) showed that the reaction was completed. The reaction mixture was cooled and quenched with a few drops of glacial acetic acid and the solvent was evaporated. The residue was taken up in methanol and analyzed by mass spectrometer [MS 368.2 (M+1) and 390.2 (M+23)].

$A_1$-agonist stimulated [$^{35}$S]GTPγS binding of several compounds of this example was determined by the method set forth in Example 1, above. The assay results are set forth in Table 2, below.

TABLE 2

| Compound # | GTPγS |
|---|---|
| CPA | 100% |
| 5 | 89% |
| 11 | 68% |
| 12 | 77% |
| 13 | 95% |

Example 4

An example of a specific synthesis of one of the compounds of this invention is shown in Scheme 4. Preparation of compound 7 starting from compound 3 is shown in scheme 3. Compound 3 was prepared from 6-chloropurineriboside 1 and 3-(R)-aminotetrahydrofuran following the procedure reported previously (See U.S. Pat. No. 5,789,164). Protection of the 2' and 3' hydroxyls with dimethoxypropane in the presence of TsOH(cat.) gave acetonide 4. Reaction of 4 with MsCl in pyridine at 0° C. gave mesylate 5 which on displacement with sodium methanethiolate in an acetonitrile/water mixture gave sulfide 6. Deprotection of 6 with 80% acetic acid/water gave the target compound 7.

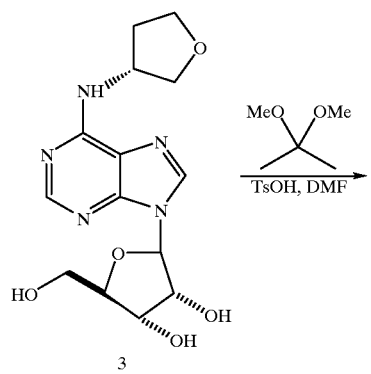

3

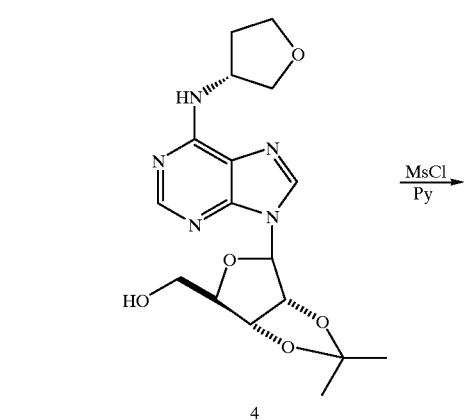

4

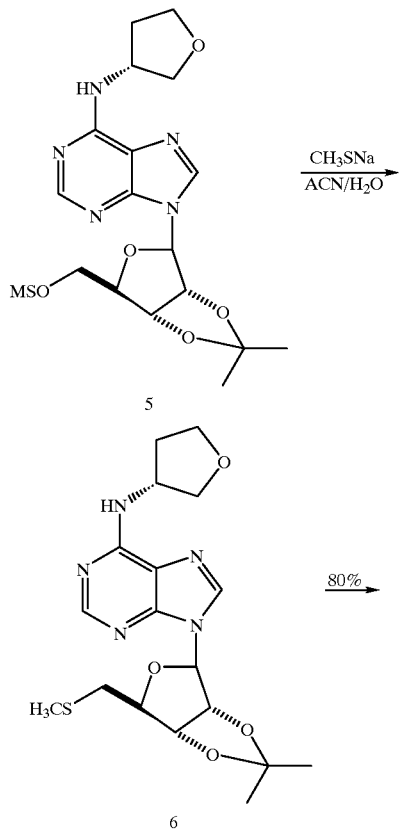

5

6

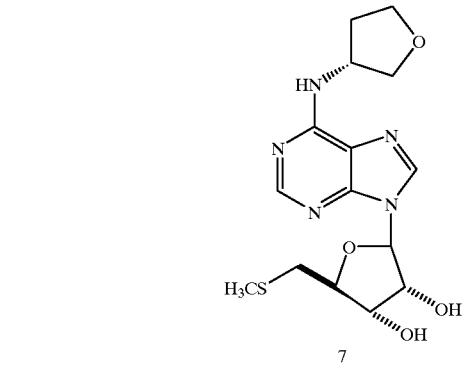

7

2-{6-[((3R)oxolan-3-yl)amino]purin-9-yl}(4S,5S,2R,3R)-5-[(Ethylthio)methyl 3,4-diol (8)

Compound 8 was prepared in the manner similar to that of 7 substituting ethane thiolate for methane thiolate. (M+1) 382.30

2-{6-[((3R)oxolan-3-yl)amino]purin-9-yl}(4S,5S,2R,3R)-5-[(Methylethylthio)methyl]oxolane-3,4-diol (10)

Compound 10 was prepared in the manner similar to that of 7 substituting i-propane thiolate for methane thiolate.

2-{6-[((3R)oxolan-3-yl)amino]purin-9-yl}(4S,5S,2R,3R)-5-(phenylthiomethyl)oxolane-3,4-diol (11)

Compound 11 was prepared in the manner similar to that of 7 substituting phenyl thiolate for methane thiolate.

2-{6-[((3R)oxolan-3-yl)amino]purin-9-yl}(4S,5S, 2R,3R)-5-[(4-Methoxyphenylthio)methyl]oxolane-3, 4-diol (12)

This compound was prepared in the manner similar to that of 7 substituting 4-methoxyphenyl thiolate for methane thiolate. (M+1)=460.4

2-{6-[((3R)oxolan-3-yl)amino]purin-9-yl}(4S,5S, 2R,3R)-5-[(4-chlorophenylthio)methyl]oxolane-3,4-diol (13)

This compound was prepared in a manner similar to that of 7 substituting 4-chlorophenyl thiolate for methane thiolate. (M+1)=464.3

2-{6-[((3R)oxolan-3-yl)amino]purin-9-yl}(4S,5S, 2R,3R)-5-[(4-fluorophenylthio)methyl]oxolane-3,4-diol (14)

This compound was prepared in a manner similar to that of 7 substituting 4-fluorophenyl thiolate for methane thiolate. (M+1)=448.3

2-{6-[((3R)oxolan-3-yl)amino]purin-9-yl}(4S,5S, 2R,3R)-5-[(4-methylphenylthio)methyl]oxolane-3,4-diol (15)

This compound was prepared in a manner similar to that of 7 substituting 4-methylphenyl thiolate for methane thiolate. (M+1)=444.38

2-{6-[((3R)oxolan-3-yl)amino]purin-9-yl}(4S,5S, 2R,3R)-5-[(4-(trifluoromethyl)phenylthio)methyl] oxolane-3,4-diol (16)

This compound was prepared in a manner similar to that of 7 substituting 4-trifluoromethylphenyl thiolate for methane thiolate. (M+1)=488.36

2-{6-[((3R)oxolan-3-yl)amino]purin-9-yl}(4S,5S, 2R,3R)-5-[(2-Methoxyphenylthio)methyl]oxolane-3, 4-diol (17)

This compound was prepared in a manner similar to that of 7 substituting 2-methoxyphenyl thiolate for methane thiolate. (M+1)=460.4

2-{6-[((3R)oxolan-3-yl)amino]purin-9-yl}(4S,5S, 2R,3R)-5-[(2,4-difluorophenylthio)methyl]oxolane-3,4-diol (18)

This compound was prepared in a manner similar to that of 7 substituting 2,4-difluorophenyl thiolate for methane thiolate. (M+1)=466.23

2-{6-[((3R)oxolan-3-yl)amino]purin-9-yl}(4S,5S, 2R,3R)-5-[(2,6-dichlorophenylthio)methyl]oxolane-3,4-diol (19)

This compound was prepared in a manner similar to that of 7 substituting 2,6-dichlorophenyl thiolate for methane thiolate. (M+1)=498.18

2-{6-[((3R)oxolan-3-yl)amino]purin-9-yl}(4S,5S, 2R,3R)-5-[(3-fluorophenylthio)methyl]oxolane-3,4-diol (20)

This compound was prepared in a manner similar to that of 7 substituting 3-fluorophenyl thiolate for methane thiolate. (M+1)=448.26

2-{6-[((3R)oxolan-3-yl)amino]purin-9-yl}(4S,5S, 2R,3R)-5-[(2-fluorophenylthio)methyl]oxolane-3,4-diol (21)

This compound was prepared in a manner similar to that of 7 substituting 2-fluorophenyl thiolate for methane thiolate. (M+1)=448.24

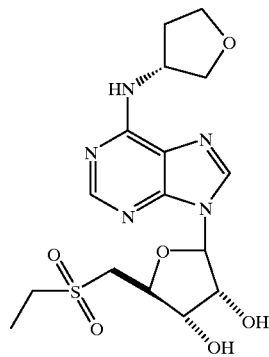

(5-{6-[((3R)oxolan-3-yl)amino]purinyl-9-yl(2S,3S, 4R,5R)-3,4-dihydroxyoxolan-2-yl)(ethylsulfonyl) methane (9)

To a cooled solution of sulfide 8 in methanol at 0° C. under nitrogen was added 3 eq. of Oxone (Potassium peroxy monosulfate) and the reaction mixture was allowed to stir at the same temperature for 1 hour. After the starting material consumed (by TLC), the reaction mixture was concentrated and filtered through a small plug of silica gel. Purification by preparative TLC [methanol-dichloromethane (1:19)] afforded 9 as an off-white hygroscopic solid. (M+1)=414.28

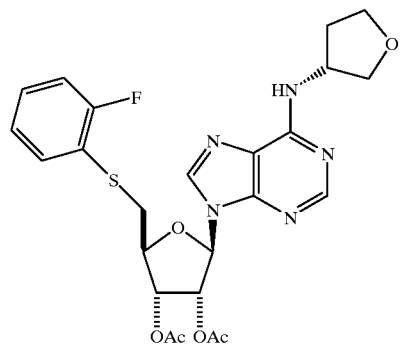

5-16-[((3R)oxolan-3-yl)amino]purin-9-yl}(2S,3R, 4R,5R)-4-acetyloxy-2-[(fluorophenylthio)methyl] oxolan-3-yl acetate (22)

To a solution of compound 21 (139 mg) in pyridine (2 mL) at 23° C. was added acetic anhydride (0.1 mL). After 3 h at 23° C., the reaction was concentrated in vacuo. The residue was dissolved in methylene chloride (50 mL), washed with water (3×10 mL), and dried (Na$_2$SO$_4$). After concentration in vacuo, the residue was purified by flash chromatography (methylene chloride:methanol 20:1 followed by 9:1) to afford compound 22 (170 mg): (M+1)= 532.23.

Methyl 2[(5-{6-[((3R)oxolan-3-yl)amino]purin-9-yl}(2S,3S,4R,5R)-3,4-dihydroxyoxolan-2-yl) methylthio]benzoate (23)

To a solution of Compound 4 (0.377 g, 1 mmol) in 5 mL of THF, was added Triphenylphosphine (0.524 g, 2 mmol), DEAD (0.40 mL, 2 mmoles), let stir for 5 minutes before adding 2-carbomethoxythiophenol (0.5 mL). Reaction was allowed to stir under reflux. After 72 h of reflux, the reaction was concentrated in vacuo and the residue purified by flash column chromatography (20%EtOAc/Hexanes) to give a clear viscous oil. It was taken into a mixture of aceticacid (8 mL) and water (2 mL) and heated at 80 C for 16 h. Solvents were removed in vacuo and the residue was purified by prep TLC [methanol-dichloromethane (1:9)] to give compound 23. (M+1)=488.5

{2[(5-{6-[((3R)oxolan-3-yl)amino]purin-9-yl}(2S, 3S,4R,5R)-3,4dihydroxyoxolan-2-yl) methylthio] phenyl}-N-methylcarboxamidebenzoate (24)

Compound 23 was taken into 40% aq.methylamine (2 mL) and I-propanol (2 mL) and heated at 70 C for 16 h. Solvents were removed in vacuo and the residue was purified by prep TLC TLC [methanol-dichloromethane (1:9)] to give compound 24. (M+1)=487.5

2-{6-[((3R)oxolan-3-yl)amino]purin-9-yl}(4S,5S, 2R,3R)-5-(benzoxazol-2-ylthiomethyl)oxolane-3,4-diol (25)

This compound was prepared in a manner similar to that of 23 substituting 2-mercaptobenzoxazole for 2-carbmethoxy thiophenol (M+1)=471.4.

2-{6-[((3S)oxolan-3-yl)amino]purin-9-yl}(4S,5S,2R, 3R)-5-[(1-yl-thio)methyl]oxolane-3,4-diol (26)

Compound 26 was prepared in the manner of compound 23 substituting 2-mercapto-1-methyl-imidazole for 2-carbomethoxythiophenol [MS 434.4 (M+1)].

2-{6-[((3S)oxolan-3-yl)amino]purin-9-yl}(4S,5S,2R, 3R)-5-(pyrimidine-2-ylthiomethyl)oxolane-3,4-diol (27)

Compound 27 was prepared in the manner of compound 23 substituting 2-mercaptopyrimidine for 2-carbomethoxythiophenol [MS 432.4 (M+1)].

2-{6-[((3S)oxolan-3-yl)amino]purin-9-yl}(4S,5S,2R, 3R)-5-(2-pyridylthiomethyl)oxolane-3,4-diol (28)

Compound 28 was prepared in the manner of compound 23 substituting 2-mercaptopyridine for 2-carbomethoxythiophenol [MS 431.4 (M+1)].

2-{6-[((3S)oxolan-3-yl)amino]purin-9-yl}(4S,5S,2R, 3R)-5-(4-pyridylthiomethyl)oxolane-3,4-diol (29)

Compound 29 was prepared in the manner of compound 23 substituting 4-mercaptopyridine for 2-carbomethoxythiophenol [MS 431.4 (M+1)].

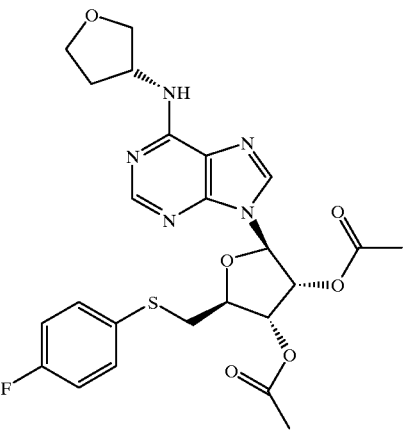

5-{6-[((3R)oxolan-3-yl)amino]purin-9-yl}(2S,3R, 4R,5R)-4-acetyloxy-2-[(4-fluorophenylthio)methyl] oxolan-3-yl]acetate (30) (M+1)=532.17.

$A_1$-agonist stimulated [$^{35}$S]GTPγS binding of several compounds of this example was determined by the method set forth in Example 1, above. The assay results are set forth in Table 3 below.

TABLE 3

| Compound # | GTPγS |
|---|---|
| CPA | 100% |
| 8 | 104% |
| 12 | 52% |
| 13 | 69% |
| 14 | 61% |
| 15 | 48% |
| 16 | 31% |
| 17 | 52% |

Example 5

This example shows that the low affinity $K_i$ value of a partial agonist reflects its effect (i.e., potency) on A-V nodal conduction time in the heart.

Partial A1 adenosine receptor agonists were identified by their effect on [$^{35}$S]GTPγS binding to G proteins and binding affinities as described in Example 1. The effect of the compounds on A-V nodal conduction time in the heart was also determined as described above. Table 4 below shows that the low $K_i$ of the compounds reflects their effects on A-V nodal conduction time (A-V NCT).

TABLE 4

| Example 2 Compound # | Example 4 Compound # | $K_i$ low (uM) | $EC_{50}$ (uM) A-V NCT |
|---|---|---|---|
| 6 | | 2.6 | 3.1 |
| 49 | | 0.9 | 1.4 |
| 45 | | 0.4 | 0.6 |
| 81 | | 0.5 | 0.6 |
| Na | 21 | 0.6 | 1.2 |

Example 6

This example describes the use of the method of this invention to identify compounds with partial adenosine A1 receptor activity.

The ability of a variety of adenosine A1 receptor agonists to stimulate [$^{35}$S]GTPγS binding to G proteins was determined as described above. The stimulation of [$^{35}$S]GTPγS binding by the agonists ranged as shown in Tables 1–3 of examples 2–4 above.

The $K_i$ of the certain compounds were also evaluated as described above. $K_i$ ranging from 221 nM to 9629 nM were obtained.

Finally, the compounds were tested for their effects on S-H intervals and the results are also shown in Table 5, below.

The method of this invention was followed to select representative compounds, such as compounds which have both activity as a partial agonist and a low binding affinity (high potency). The compounds have no effect on ventricular or the atrial monophasic action potential or coronary conductance, which are adverse consequences of treatment with many adenosine A1 agonists.

TABLE 5

| Example 2 Compound # | Example 4 Compound # | $K_i$, (nM) | GTPγS (% of CPA) | $EC_{50}$ nM | S-H interval n Efficacy** |
|---|---|---|---|---|---|
| CPA | | na* | 100 | na | Full (Potent) |
| | 19 | 1340 | 89 | | Full (>2759) |
| 47 | | 1368 | 84 | | Full (>2759) |
| 46 | | 1111 | 77 | | Full (Weak) |
| 45 | | 346 | 77 | 570 | Partial |
| 13 | | 1096 | 77 | | Partial (= 2759) |
| 6 | | 953, 3000 | 76 | | Partial (2700) |
| 69 | | >1458 (P Sol) | 69 | | Partial (= 2759) |
| 81 | | 1107 | 84 | 530 | Partial |
| 83 | | 443 | 77 | 610 | Partial |
| | 21 | 372, 221 | 72 | 1260 | Partial (>2759) |
| | 20 | 1559 | 84.2 | | Partial (= 2759) |
| 49 | | 895 | 89 | | Partial |
| 27 | | 9629 | 44 | | No activity |

Example 7

This example compares the binding of Compound 6 of Example 2 with CPA in the binding affinity assay of Example 1.

Figure 2A:
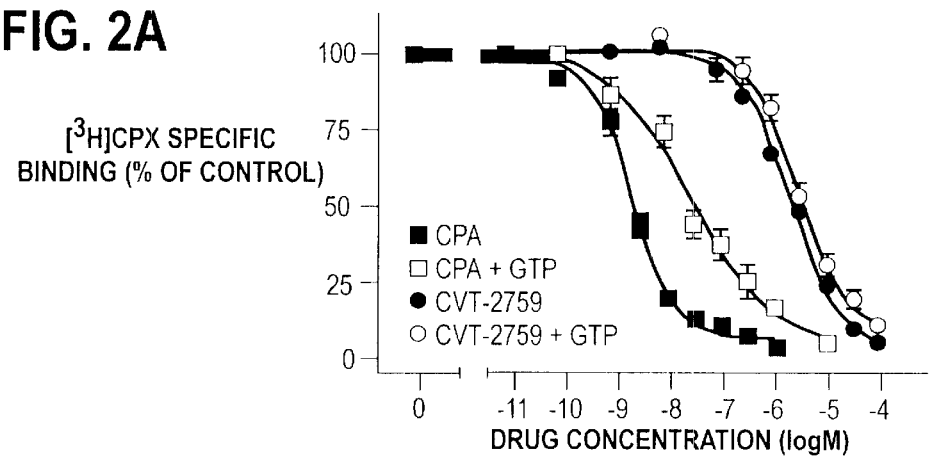
FIG. 2A. Reduction of the binding of $^3H$-CPX to guinea pig forebrain membranes caused by the $A_1$-adenosine receptor agonists Compound 6 of Example 2 and CPA in the absence and presence of 1 mM GTP. Inhibitory binding constant ($K_i$) values were calculated from those of $IC_{50}$ according to Cheng and Prusoff equation (Cheng and Prusoff, Biochem. Pharmacol, 22:3099 (1973), the contents of which are hereby incorporated by reference, $K_i = IC_{50}/(1+[C^*]/K_d^*)$, where $[C^*]$ is the concentration of radioligand and $K_d^*$ is its dissociation constant. Values of $K_i$ and Hill slope for reduction by Compound 6 of Example 2 of $^3H$-CPX binding in the absence and presence of GTP were 1.8 μM (95% confidence intervals, 1.4 to 2.3 μM) and 0.79, and 2.1 μM (95% confidence intervals, 1.4 to 3.2 μM) and 0.99, respectively. Values of $K_i$ and Hill slope for reduction by CPA of $^3$H-CPX binding in the absence of GTP were 1.7 nM (95% confidence intervals, 1.3 to 2.3 nM) and 1.2. In the presence of GTP, the Hill slope was 0.53, and the value(s) of $K_1$ for CPA were therefore calculated using a 2-site binding model with 73% of sites having a high affinity for CPA. Values of $K_i$ for CPA for the high and low affinity sites in the presence of GTP were 10.4 and 882 nM, respectively. The mean values of concentrations of $^3$H-CPX in experiments with Compound 6 of Example 2 and CPA were 0.58 and 0.66 nM, respectively. Symbols represent the mean and SE of 3–4 determinations in each of 5–6 experiments.

Compound 6 of Example 2 and CPA reduced the binding of $^3$H-CPX to forebrain membranes (FIG. 2A). The affinity of compound 6 of Example 2 for $A_1$-AdoRs in guinea pig forebrain membranes was slightly but not significantly reduced by 1 mM GTP (FIG. 2A). The values of $IC_{50}$ for compound 6 of Example 2 to reduce the binding of $^3$H-CPX in the absence and presence of GTP were 2.5 AM (95% confidence intervals, 1.9–3.3 μM) and 2.9 μM (95% confidence intervals, 1.9–4.5 μM), respectively (P=NS). In contrast, the values of $IC_{50}$ for CPA to reduce the binding of $^3$H-CPX to forebrain membranes in the absence and presence of 1 mM GTP were 11-fold different: 2.5 nM (95% confidence intervals, 1.8–3.4 μM) and 28 nM (95% confidence intervals, 7.8–102 nM), respectively (P<0.05). The monophasic reduction of the binding of $^3$H-CPX by compound 6 of Example 2 may be interpreted to indicate that compound 6 of Example 2 bound to G protein-coupled and uncoupled $A_1$-AdoRs with a single low affinity. In contrast, CPA appeared to bind with a single high affinity to nearly all $A_1$-AdoRs.

Figure 2B:
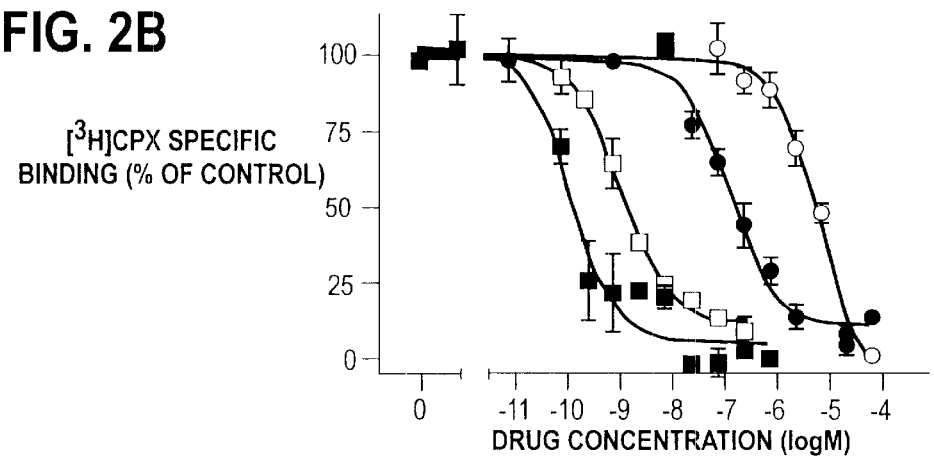
FIG. 2B. Reduction of the binding of $^3$H-CPX to rat adipocyte membranes caused by Compound 6 of Example 2 and CPA in the absence and presence of 1 mM GTP. Values of $K_i$ and Hill slope for reduction by Compound 6 of Example 2 of $^3$H-CPX binding in the absence and presence of GTP were 62 nM (95% confidence intervals, 35–108 nM) and 0.87, and 3.3 $\mu$M (95% confidence intervals, 2.1–5.3 $\mu$M) and 1.0, respectively. Values of $K_i$ and Hill slope for reduction by CPA of $^3$H-CPX binding in the absence and presence of GTP were 0.052 nM (95% confidence limits, 0.02–0.11 nM) and 0.88, and 0.52 nM (95% confidence limits, 0.40–0.66 nM) and 1.0, respectively. The mean values of concentrations of $^3$H-CPX in experiments with Compound 6 of Example 2 and CPA were 0.75 and 0.80 nM, respectively. Assays were done as described in Methods. Symbols represent the mean and SE of 3 (for CPA) or 6 (for Compound 6 of Example 2) determinations in each of 4 (CPA) or 5 (Compound 6 of Example 2) experiments.

Results of binding assays using rat adipocyte membranes differed from results of assays using guinea pig brain membranes (FIG. 2B). Whereas the values of $IC_{50}$ for compound 6 of Example 2 to reduce the binding of $^3$H-CPX to brain membranes in the absence and presence of GTP were not significantly different, the values of $IC_{50}$ for compound 6 of Example 2 to reduce the binding of $^3$H-CPX to adipocyte membranes in the absence and presence of GTP were 53-fold different. The values of $IC_{50}$ for compound 6 of Example 2 to reduce the binding of $^3$H-CPX in the absence and presence of 1 mM GTP were 0.18 μM (95% confidence intervals, 0.10–0.31 μM) and 9.5 μM (95% confidence intervals, 5.9–15.3 EM), respectively (FIG. 2B). Reduction by CPA of binding of $^3$H-CPX to adipocyte membranes in the absence and presence of GTP was similar to reduction of binding of $^3$H-CPX to brain membranes. The values of $IC_{50}$ for reduction by CPA of $^3$H-CPX binding to adipocyte membranes in the absence and presence of 1 mM GTP were 10-fold different: 0.15 and 1.5 nM, respectively, P<0.05 (95% confidence limits, 0.07–0.32 and 1.2–2.0 nM, respectively). Thus, GTP caused a greater reduction of the binding of compound 6 of Example 2 than of CPA. A possible explanation for this unexpected finding is that the uncoupling effect of GTP (i.e, $A_1$-AdoR uncoupling from G proteins) was incomplete and was antagonized more by the strong agonist CPA than by the weak agonist compound 6 of Example 2. Indeed, when adipocyte membranes were incubated with 1 mM GTP and 0.1 mM N-ethylmaleimide, a more complete uncoupling of $A_1$AdoR from G proteins appeared to be achieved, in comparison to that caused by GTP alone. The value of $IC_{50}$ for reduction by CPA of $^3$H-CPX binding to adipocyte $A_1$-AdoR was 22-fold higher in the presence of both GTP and N-ethylmaleimide than in the presence of GTP alone (33 vs. 1.5 μM, P<0.05, not shown). In contrast, the value of IC50 for reduction by compound 6 of Example 2 of $^3$H-CPX binding to adipocyte $A_1$-AdoR was only 1.6-fold higher in the presence of GTP and N-ethylmaleimide than in the presence of GTP alone (15 vs. 9.5 μM, P=NS). Thus, when rat adipocyte membranes are incubated with GTP, a stronger coupling of $A_1$-AdoR to G proteins occurs in the presence of CPA than in the presence of compound 6 of Example 2.

Example 8

This example evaluated the effect of compound 6 of Example 2 on Isolated Guinea Pig Hearts.

Isolation and Ex vivo Culture of Hearts

Guinea pigs (Hartley) of either sex weighing 300–350 g were anaesthetized with methoxyflurane and killed by decapitation. The chest was cut open and the heart was removed quickly and rinsed in ice-cold modified Krebs-Henseleit (K-H) solution. The contents of the modified K-H solution were (in mM): NaCl 117.9, KCl 4.8, $CaCl_2$ 2.5, $MgSO_4$ 1.18, $KH_2PO_4$ 1.2, $Na_2$ EDTA 0.5, ascorbic acid 0.14, dextrose 5.5, pyruvic acid (sodium salt) 2.0, and $NaHCO_3$ 25. The K-H solution was continuously gassed with 95% oxygen and 5% $CO_2$, and the pH was adjusted to a value of 7.4. To perfuse the heart by the Langendorff method, the transected aorta was slid onto a glass cannula and secured by a ligature. Retrograde perfusion of the aorta was initiated immediately at a constant flow of 10 ml min-' with modified K-H solution warmed to 36.0±0.5° C. A side port in the cannula was used to connect the perfusion line to a Gould pressure transducer for measurement of coronary perfusion pressure. Coronary perfusion pressure was continuously recorded on a strip chart (Gould RS3400, Cleveland, Ohio) throughout each experiment. Coronary conductance (in ml min$^{-1}$ mmHg$^{-1}$) was calculated as the ratio of coronary flow (10 ml min$^{-1}$) to perfusion pressure (mm Hg). To facilitate the exit of fluid from the left ventricle, the leaflets of the mitral valve were trimmed with fine spring-handled scissors. When appropriate, hearts were paced at a constant rate using external electrodes. After completion of dissection and instrumentation (see below) for measurement of either atrial rate, stimulus-to-His bundle (S-H) interval, monophasic action potentials, or coronary perfusion pressure, each heart was allowed to equilibrate for 20–40 min before the administration of drug. Experimental interventions were always preceded and followed by control measurements. Criteria for exclusion of hearts from study were (1) a coronary perfusion pressure of less than 50 mm Hg, (2) absence of a stable coronary perfusion pressure during the equilibration period, and (3) inability to pace a heart at a constant rate throughout an experiment.

For electrical pacing of hearts, a bipolar teflon™-coated electrode was placed in the wall of the intra-atrial septum. Parts of the left and right atrial tissues including the region of the sinoatrial node were removed, both to decrease the spontaneous heart rate and to expose the atrial septum for electrode placement. Hearts were electrically paced at a fixed cycle length of 280–300 msec. Stimuli were provided by an interval generator (Model 1830, WPI, Sarasota, Fla.) and delivered through a stimulus isolation unit (Model 1880, WPI) as square wave pulses of 3 msec in duration and at least twice threshold intensity.

Prolongation of the S-H interval was used as a measure of the negative dromotropic effect of $A_1$-AdoR agonists on AV nodal conduction. Hearts were paced at a constant cycle length of from 280 to 300 msec as described above. The His bundle electrogram was recorded from a unipolar electrode placed in the right side of the inter-atrial septum adjacent to the atrioventricular junction. The signal was displayed continuously in real time on an oscilloscope screen at a sweep rate of 10 msec/cm. The duration of time from the first pacing artifact to the maximum upward deflection of the His bundle signal was used as the S-H interval.

Compound 6 of Example 2 slowed AV nodal conduction without causing second-degree AV block and caused minimal slowing of the atrial rate of the guinea pig isolated heart (FIG. 3). In contrast, the full agonist CPA caused markedly greater slowing of both AV nodal conduction and atrial rate than did compound 6 of Example 2 (FIG. 3). Compound 6 of Example 2 increased the S-H interval of the electrically paced heart in a concentration-dependent manner by a maximum of 33%, from 45±1 to 60±3 msec (P<0.01) with an $EC_{50}$ value of 3.1 μM (95% confidence intervals, 2.1 and 4.7 μM) (FIG. 3A). Compound 6 of Example 2 did not cause second-degree A-V block in any heart. The effect of compound 6 of Example 2 on the S-H interval appeared to reach a maximum at 30–100 μM. Low concentrations of CPA (<20 nM) caused stable, reversible increases of the S-H interval (FIG. 3A). Comparable submaximal responses (an increase of the S-H interval by 13 msec) occurred at CPA and compound 6 of Example 2 concentrations of 10 and 10,000 nM, respectively (FIG. 3A). Higher concentrations of CPA (>20 μM) caused the S-H interval to prolong rapidly, culminating in AV block. CPA (30 nM) increased the S-H interval from 44±1 to 87±2 msec (P<0.01) and caused second-degree AV block in all hearts. Compound 6 of Example 2 and CPA had markedly different effects on the atrial rate of isolated, spontaneously-beating hearts (FIG. 4B). Compound 6 of Example 2 decreased the atrial rate by only 13%, from 195±6 to 169±7 beats per minute (P<0.05), whereas CPA decreased the atrial rate from 198±15 to 1±1 beats per minute (FIG. 3B) with an $EC_{50}$ value of 68 nM (95% confidence intervals, 57 and 80 nM).

The full $A_1$-AdoR antagonist CPX (50 nM) significantly reversed the S-H interval prolongation induced by 10 μM compound 6 of Example 2 (not shown). Compound 6 of Example 2 (10 μM) caused a 12-msec increase of the S-H interval from 46±2 to 58±2 msec (n=7, P<0.05). However, compound 6 of Example 2 (10 μM) caused only a 4-msec increase of the S-H interval in the presence of 50 nM CPX (i.e., the S-H interval was reduced from 58±2 to 50±2 msec [n=7, P<0.05] by CPX in the continued presence of compound 6 of Example 2).

In order to show that adenosine shortens the duration of the atrial action potential, a bolus (100 μl) of 1 mM adenosine was administered at the end of an experiment to confirm the responsiveness of each preparation. Adenosine shortened the duration of the atrial monophasic action potential at 90% of repolarization to 22±5 msec (n=4, P<0.05 vs control and compound 6 of Example 2).

A partial agonist will competitively antagonize the response to a fall agonist To confirm the partial agonist nature of compound 6 of Example 2, we measured the responses of the guinea pig isolated heart to the full agonists CPA and adenosine in the absence and presence of 10 μM compound 6 of Example 2. As shown in FIG. 4, CPA significantly prolonged the S-H interval at concentrations of 10, 15, and 20 μM from a control value of 42±1 msec to 59±4, 81±6, and 103±8 msec, respectively. Compound 6 of Example 2 (10 μM) partially reversed the S-H interval prolongation induced by CPA. The antagonism by 10 μM compound 6 of Example 2 of the S-H interval prolongation caused by CPA was greater in the presence of 20 nM CPA than in the presence of 15 or 10 nM CPA (FIG. 4).

Consistent with its antagonism of the effect of CPA, compound 6 of Example 2 shifted the concentration-response relationship for adenosine to prolong S-H interval significantly to the right (FIG. 5, n=4, P<0.01 by two-way ANOVA). In the absence of compound 6 of Example 2, adenosine prolonged the S-H interval in concentration-dependent manner and caused second-degree AV block at a concentration of 6 μM. In the presence of 4 and 10 μM compound 6 of Example 2, adenosine caused second-degree AV block at concentrations of 8 and 20 μM (FIG. 5). Thus, the concentration of compound 6 of Example 2 that would cause a 2-fold shift (i.e., the $pA_2$ value for compound 6 of Example 2) of the adenosine concentration-response relationship appears to be greater than 4 but less than 10 μM.

Samples (5 ml each) of the coronary effluent of isolated guinea pig hearts were collected during the last minute of a control or drug treatment period and stored at −80° C. until analysis of adenosine content by HPLC. The HPLC system included a Spectra-Physics 8800 pump, 8490 UV detector, and 4290 integrator, a Rainin injection valve, and a Luna 5 μm particle size, C-18(2) column with a diameter of 4.6 mm and a length of 250 mm (Phenomenex, Torrance, Calif.). Samples and standards (10 pmol of adenosine) of 100-μl volume were manually injected onto the column and eluted with a solution of 50 mM $KH_2PO_4/K_2HPO_4$ buffer, pH 6.5, with 15% methanol, at a rate of 1.5 ml/min at room temperature. Adenosine content of samples was determined by quantification of peak height and comparison to the peak height recorded for a 10-pmol standard. A standard was assayed after analysis of every fifth sample. All samples were filtered (0.22 μm) before injection onto the HPLC column.

If compound 6 of Example 2 antagonizes the actions of exogenous CPA and adenosine, then it should also antagonize the action of endogenous adenosine in the heart. Treatment of hearts with inhibitors of adenosine kinase and adenosine deaminase has been demonstrated to cause an increase of the interstitial adenosine concentration. Therefore, the adenosine kinase inhibitor iodotubercidin (1 μM) and the adenosine deaminase inhibitor EHNA (200 nM) were used in this study to cause an elevation of endogenous adenosine. Simultaneous administration of the two agents into the coronary perfusate of isolated hearts increased the adenosine concentration in the coronary effluent from 11±2 to 65±5 nM (n=6, P<0.01). Concomitantly, the S-H interval increased by 34±6 msec from 46±1 to 80±6 msec (FIG. 6). In the presence of iodotubercidin and EHNA, 10 μM compound 6 of Example 2 decreased the S-H interval significantly by 16 msec from 80±6 to 64±2 msec (FIG. 6).

The concentration of adenosine in the coronary effluent did not change during administration of 10 μM compound 6 of Example 2 and remained at 65±9 μM (n=6).

Compound 6 of Example 2 also increased the coronary conductance of the guinea pig isolated heart. Analysis of concentration (9 concentrations from 0.01 to 100 μM)-response data from 4 experiments indicated that compound 6 of Example 2 at concentrations ≦10 μM did not significantly change the coronary conductance (not shown). Compound 6 of Example 2 increased coronary conductance in a concentration-dependent manner at concentrations between 10–100 μM. Values of coronary conductance increased from a control of 0.17±0.01 to 0.185±0.01 and 0.26±0.02 ml min$^{-1}$ mmHg$^{-1}$ (n=4, P<0.05 vs control) in the presence of 10 and 100 μM compound 6 of Example 2, respectively. From these data, a half-maximal response to compound 6 of Example 2 was calculated to occur at a concentration of 31 μM. However, because a maximal response to compound 6 of Example 2 may not have been achieved in these experiments due to limited solubility of compound 6 of Example 2, this estimate of the $EC_{50}$ value for compound 6 of Example 2 to cause an increase of coronary conductance may be falsely low. Nonetheless, these data suggest that compound 6 of Example 2 is >10 times more potent as a negative dromotropic agent (i.e., to increase the S-H interval) than as a coronary vasodilator. The relatively selective $A_1$-AdoR agonist CPA also increased coronary conductance of the guinea pig isolated heart. Both the potency and maximal effect of CPA were greater than those of compound 6 of Example 2. CPA increased coronary conductance in a concentration-dependent manner from 0.16±0.01 to 0.33±0.01 (n=4) ml min$^{-1}$ mmHg-$^1$ (P<0.001). A half-maximal increase of coronary conductance occurred at 71 nM CPA (95% confidence limits, 59–86 nM). Thus, CPA was at least 400 times more potent than compound 6 of Example 2 as a coronary vasodilator. The maximal increases of coronary conductance of 0.15±0.02 and 0.17±0.02 ml min$^{-1}$ mmHg$^{-1}$ caused by adenosine in a previous study (12) and CPA in this study were significantly greater than the 0.09±0.01 ml min$^{-1}$ mmHg$^{-1}$ increase of coronary conductance caused by 100 μM compound 6 of Example 2 in the present study. Thus, either compound 6 of Example 2 is not a full agonist to increase coronary conductance, or a maximal response to compound 6 of Example 2 occurs at a higher concentration than was used here (100 μM).

To measure spontaneous atrial rate in hearts that were not paced, a unipolar electrode was placed on the right atrium. A total of 10 atrial beats before, during, and after each intervention was recorded on chart paper moving at a rate of 50 mm per sec, and the average atrial rate at each time was determined from these records.

Monophasic action potential durations in atrial and ventricular regions of the heart were recorded using two pressure-contact silver—silver chloride electrodes (Langendorff Probe, EP Technologies, Inc., Sunnyvale, Calif.) placed on the surface of the left atrium and the inferior wall of the left ventricle, respectively. The signals from the His bundle, left atrium and left ventricle were amplified and filtered by an isolated biological digital amplifier (ISODam, WPI) and displayed in real time on a computer screen. Signals were considered adequate if they were stable for at least 5–10 min and the amplitudes exceeded 10 mV. The data were digitized at 2 kHz by a DT-2801A digitizing board (Data Translation, Marlboro, Mass.) and were saved for analysis using the Snapshot data acquisition program (Snapshot Storage Scope, HEM Data Corp., Southfield, Mich.). The duration of the atrial and ventricular monophasic action potentials was measured from onset of depolarization to either 50 or 90% of repolarization.

Compound 6 of Example 2 had no significant effect on the duration of either the ventricular or the atrial monophasic action potential in the guinea pig isolated heart. The durations of the ventricular monophasic action potential at 90% of repolarization in the absence and presence of 20 μM compound 6 of Example 2 were 158±4 and 160±7 msec, respectively (n=4, P>0.05). The durations of the atrial monophasic action potential at 50 and 90% of repolarization were 41±3 and 66±4 msec in the absence of compound 6 of Example 2 and 41±3 and 74±4 msec in the presence of 20 μM compound 6 of Example 2 (n=4, P>0.05). Because it is known that adenosine shortens the duration of the atrial action potential (3), a bolus (100 μl) of 1 mM adenosine was administered at the end of an experiment to confirm the responsiveness of each preparation. Adenosine shortened the duration of the atrial monophasic action potential at 90% of repolarization to 22±5 msec (n=4, P<0.05 vs control and compound 6 of Example 2).

We claim:

1. A method for identifying compounds that are partial adenosine A1 receptor agonists useful for treating arrhythmia comprising the steps of:
   a. measuring the agonist stimulated [$^{35}$S]GTPγS binding to G proteins of guinea pig cortical membranes by said compound;
   b. measuring the extent of agonist stimulated [$^{35}$S]GTPγS binding to G proteins of guinea pig cortical membranes by a full adenosine A1 receptor agonist; and
   c. selecting those compounds with 65%–95% binding compared to said full agonist.

2. The method of claim 1 wherein said full agonist is $N^6$ cyclopentyladenosine.

3. The method of claim 1, wherein said partial agonists further have a binding affinity to the adenosine A1 receptor that is less than 3 uM.

4. The method of claim 3 wherein said binding affinity to the adenosine $A_1$ receptor is less than or equal to 1 uM.

5. The method of claim 1 wherein said agonist stimulated $^{35}$[S]GTPγS binding to G-proteins of guinea pig cortical membranes is at least 75% of the full agonist.

6. A method of predicting the effects of a compound on activities mediated by the adenosine $A_1$ receptor comprising the steps of:
   a. measuring the agonist stimulated $^{35}$[S]GTPγS binding to G proteins of guinea pig cortical membranes by said compound;
   b. measuring the extent of agonist stimulated $^{35}$[S]GTPγS binding to G proteins of guinea pig cortical membranes by a full adenosine $A_1$ receptor agonist;
   c. selecting those compounds with 65%–95% binding compared to said full agonist and;
   d. eliminating compounds with $K_i$>3.

7. The method of claim 6 wherein compounds are eliminated with $K_1 \geq 1$.

8. The method of claim 6 wherein said adenosine $A_1$ receptors are in the heart.

* * * * *